US009821027B2

(12) United States Patent
Iwasaki et al.

(10) Patent No.: US 9,821,027 B2
(45) Date of Patent: Nov. 21, 2017

(54) METHOD FOR REGENERATING CARTILAGE COMPRISING APPLYING A MONOVALENT METAL SALT OF ALGINIC ACID AND SDF-1

(71) Applicants: Mochida Pharmaceutical Co., Ltd., Tokyo (JP); National University Corporation Hokkaido University, Hokkaido (JP)

(72) Inventors: Norimasa Iwasaki, Hokkaido (JP); Atsushi Sukegawa, Hokkaido (JP); Akio Minami, Hokkaido (JP); Nobuo Ohzawa, Tokyo (JP)

(73) Assignees: Mochida Pharmaceutical Co., Ltd., Tokyo (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 14/944,357

(22) Filed: Nov. 18, 2015

(65) Prior Publication Data

US 2016/0067309 A1 Mar. 10, 2016

Related U.S. Application Data

(63) Continuation of application No. 14/239,663, filed as application No. PCT/JP2012/071749 on Aug. 22, 2012, now abandoned.

(30) Foreign Application Priority Data

Aug. 23, 2011 (JP) .................................. 2011-181662

(51) Int. Cl.
| | |
|---|---|
| *A61K 38/16* | (2006.01) |
| *A61K 38/17* | (2006.01) |
| *A61K 38/18* | (2006.01) |
| *A61K 38/19* | (2006.01) |
| *A61L 27/20* | (2006.01) |
| *A61L 27/54* | (2006.01) |
| *A61K 31/734* | (2006.01) |

(52) U.S. Cl.
CPC .......... *A61K 38/195* (2013.01); *A61K 31/734* (2013.01); *A61L 27/20* (2013.01); *A61L 27/54* (2013.01); *A61L 2300/252* (2013.01); *A61L 2300/414* (2013.01); *A61L 2430/06* (2013.01)

(58) Field of Classification Search
None
See application file for complete search history.

(56) References Cited

U.S. PATENT DOCUMENTS

| 8,435,953 B2 | 5/2013 | Tabata |
| 2008/0206302 A1 | 8/2008 | Sittinger et al. |
| 2009/0285785 A1 | 11/2009 | Jimi et al. |
| 2010/0015102 A1 | 1/2010 | Iwasaki et al. |
| 2010/0267612 A1 | 10/2010 | Tabata |
| 2010/0272679 A1 | 10/2010 | Penn et al. |

FOREIGN PATENT DOCUMENTS

| WO | WO 2007/003324 A2 | 1/2007 |
| WO | WO 2008/102855 A1 | 8/2008 |
| WO | WO 2009/060608 A1 | 5/2009 |
| WO | WO 2010/048418 A1 | 4/2010 |

OTHER PUBLICATIONS

Kitaori et al,. "Recruitment of Mesenchymal Stem Cells Upon Bone Healing: Functional Role of chemokine," The Annual Meeting of the Japanese Society for Bone and Mineral Research, Program & Abstract, 2009, 27th, 160, with English translation.

Kitaori et al., "Stromal Cell-Derived Factor 1/CXCR4 Signaling is Critical for the Recruitment of Mesenchymal Stem Cells to the Fracture Site During Skeletal Repair in a Mouse Model," Arthritis & Rheumatism, Mar. 2009, 60(3):813-823.

Kitaori et al., "Chemokine Molecule, Stromal Cell-Derived Factor 1 (SDF-1), That Promotes Bone Healing," Rinsyo Seikei Geka (Clinical orthopedic surgery), 2010, 45:72-75, with English translation.

Lu et al., "Expression of Stromal Cell-Derived Factor-1 After Articular Cartilage Injury," Zhongguo Zuzhi Gongcheng Yanjiu Yu Linchuang Kangfu (Journal of Clinical Rehabilitative Tissue Engineering Research) Jul. 2, 2011, 15(27):5063-5067, with English translation.

Mazzetti et al., "A Role for Chemokines in the Induction of Chondrocyte Phenotype Modulation", Arthritis & Rheumatism, Jan. 2004, 50(1):112-122.

Wei et al., "Chondrocyte Death Induced by Pathological Concentration of Chemokine Stromal Cell-Derived Factor-1," The Journal of Rheumatology, 2006, 33(9):1818-1826.

*Primary Examiner* — Elizabeth C Kemmerer
(74) *Attorney, Agent, or Firm* — Foley & Lardner LLP

(57) ABSTRACT

A novel composition for regenerating a cartilage has been demanded, which can achieve a good effect of regenerating a hyaline cartilage that is a nearly normal cartilage without requiring the use of any transplanted cell. The present invention provides a composition for regenerating a cartilage, wherein (a) a monovalent metal salt of low endotoxin alginic acid and (b) SDF-1 are used in combination.

18 Claims, 8 Drawing Sheets

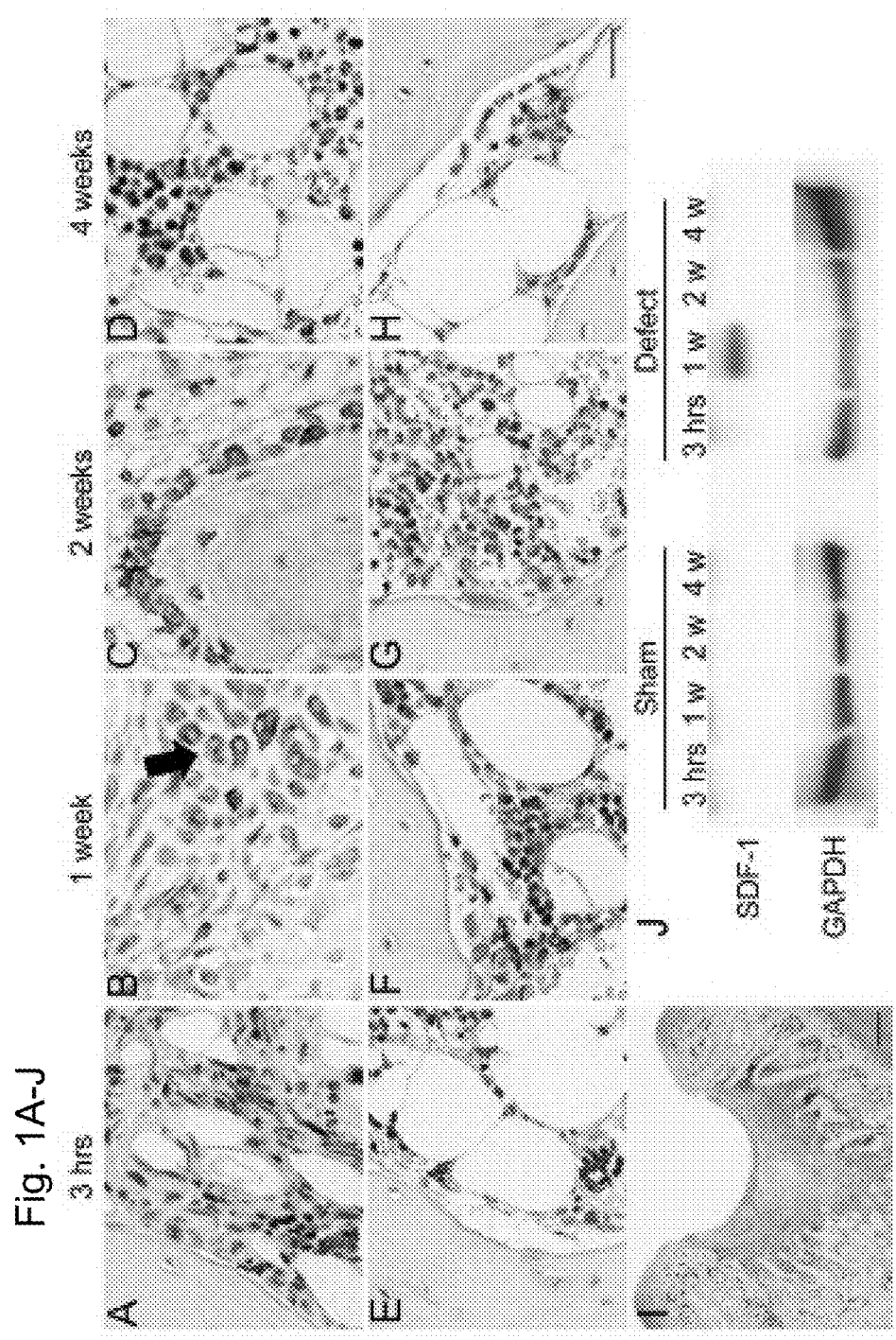
Fig. 1A-J

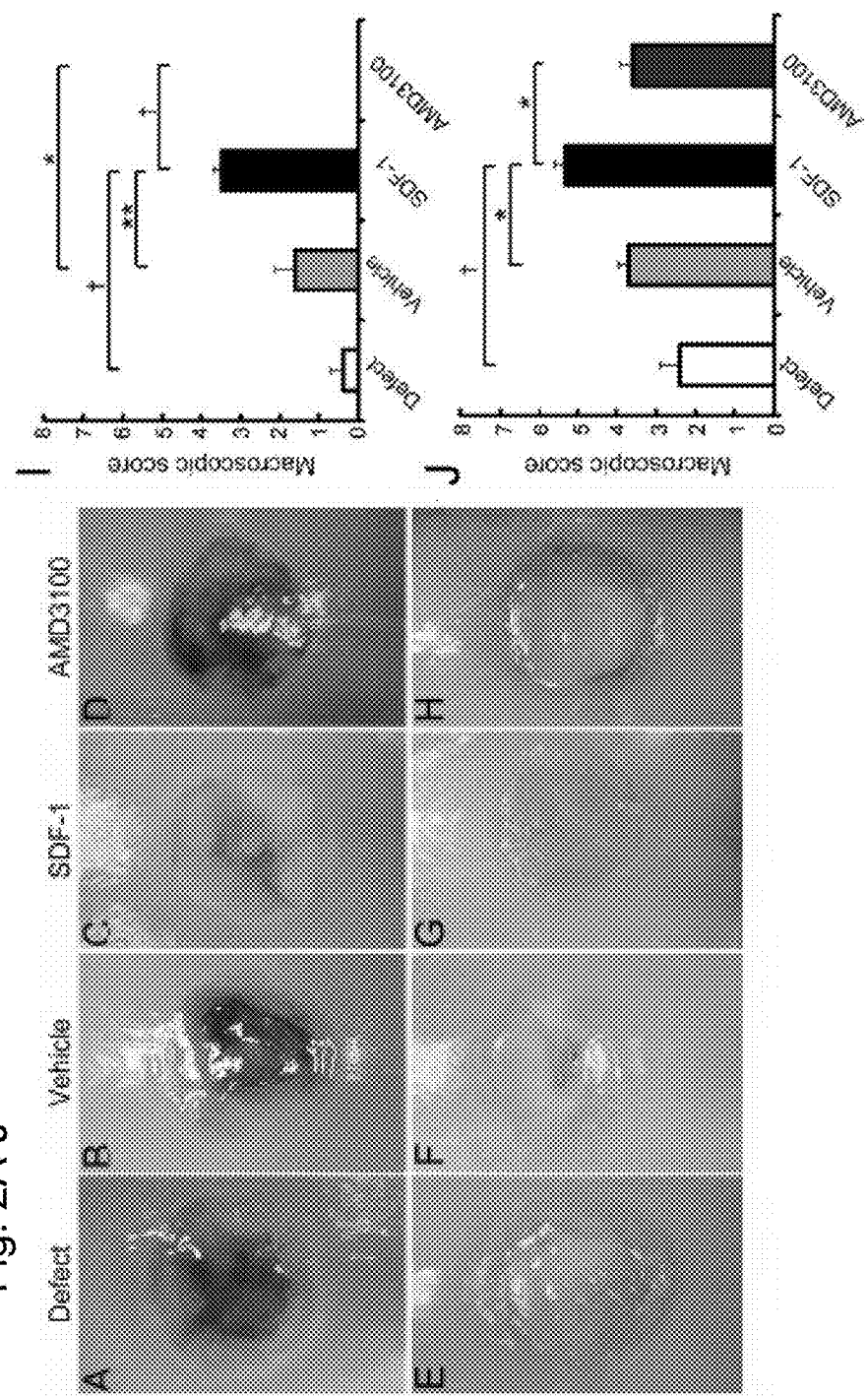
Fig. 2A-J

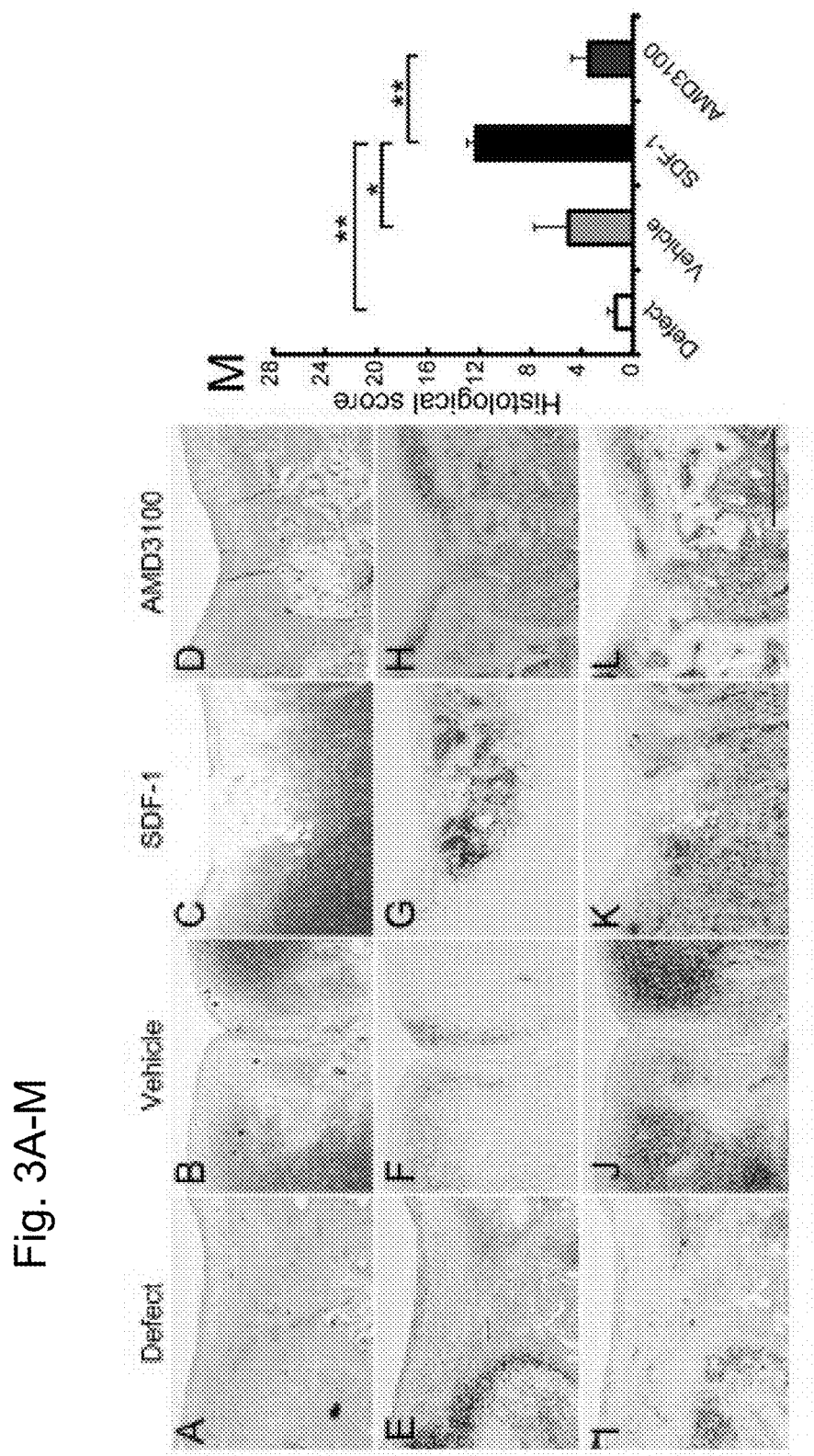
Fig. 3A-M

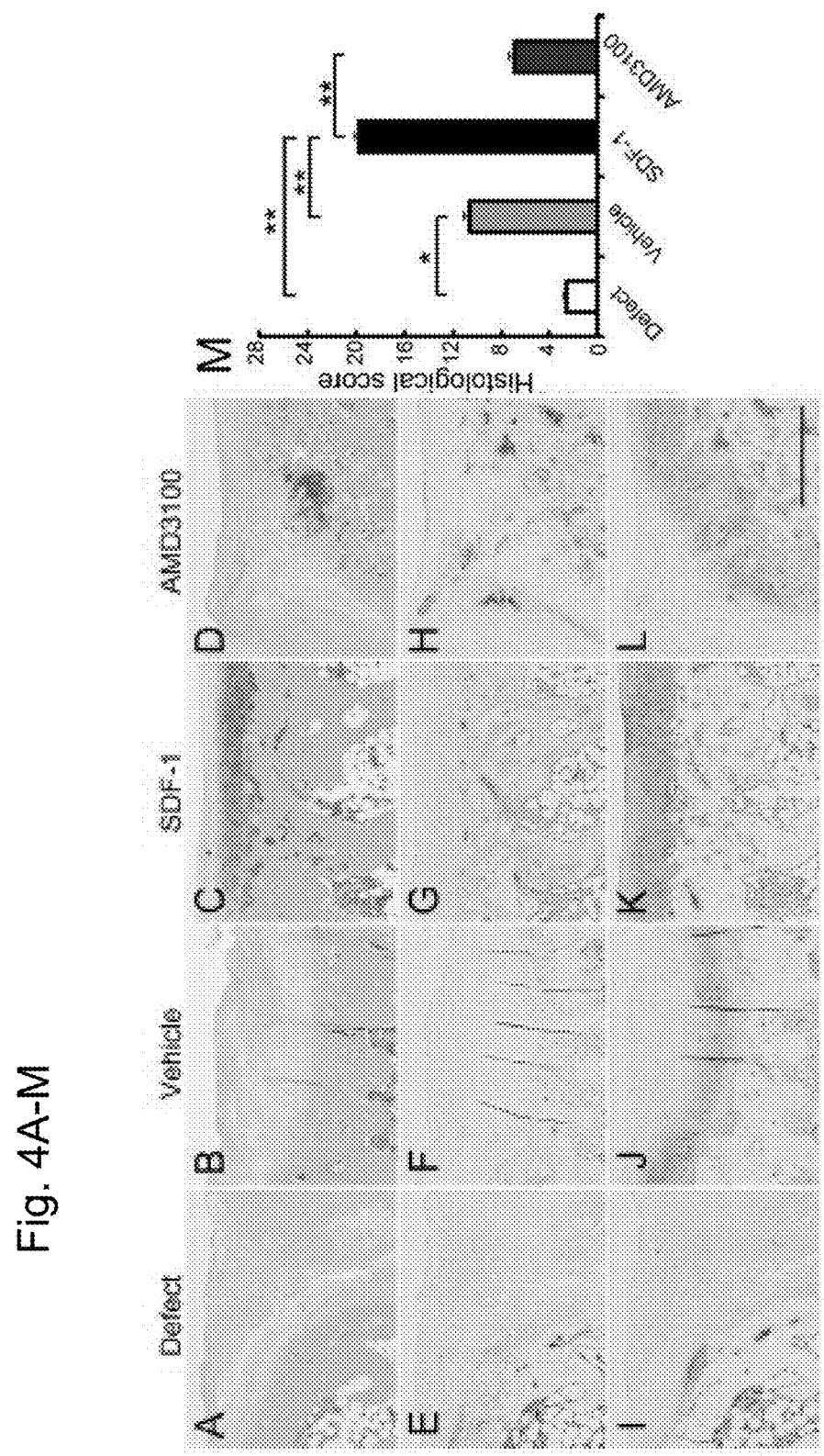
Fig. 4A-M

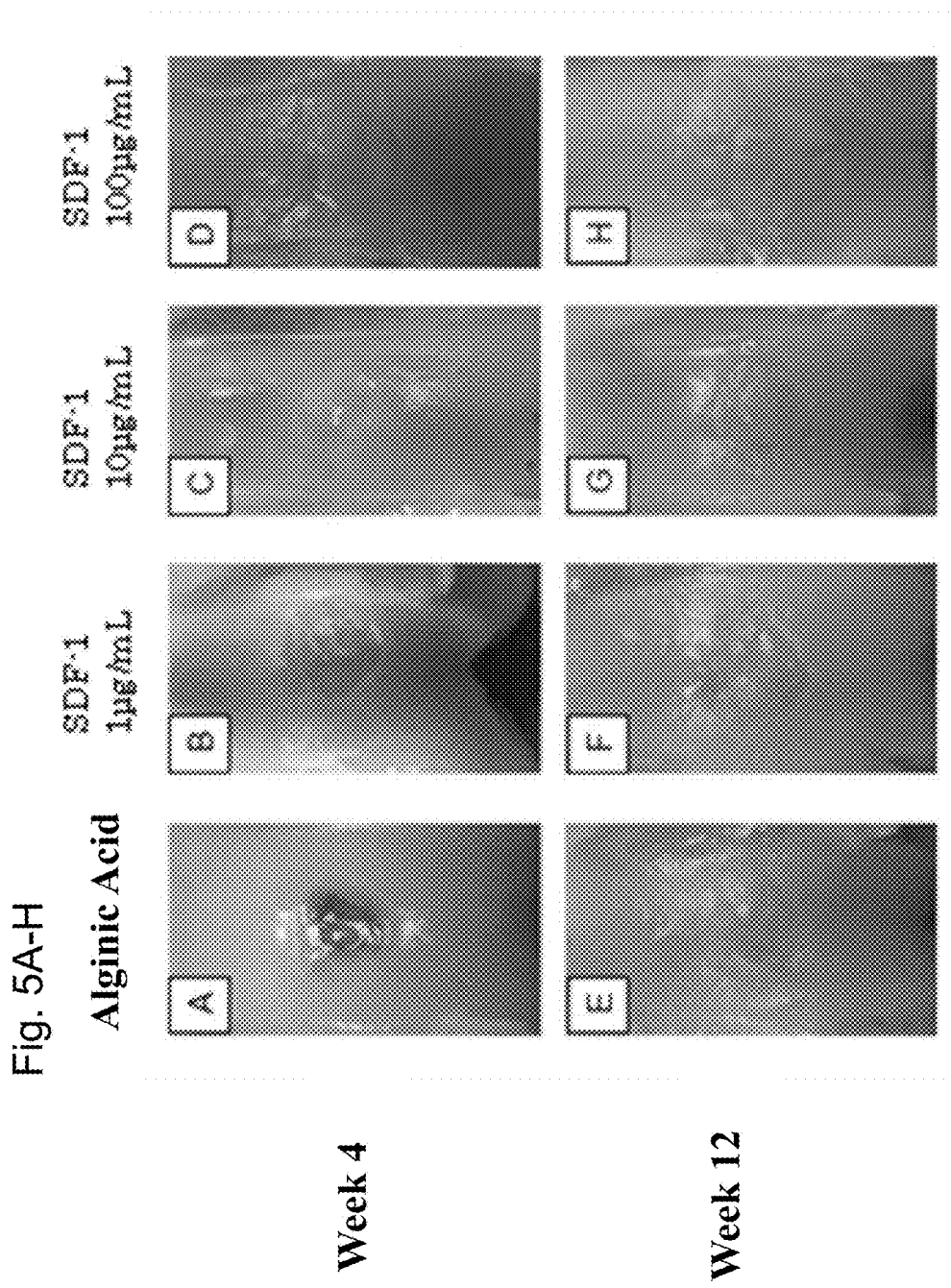

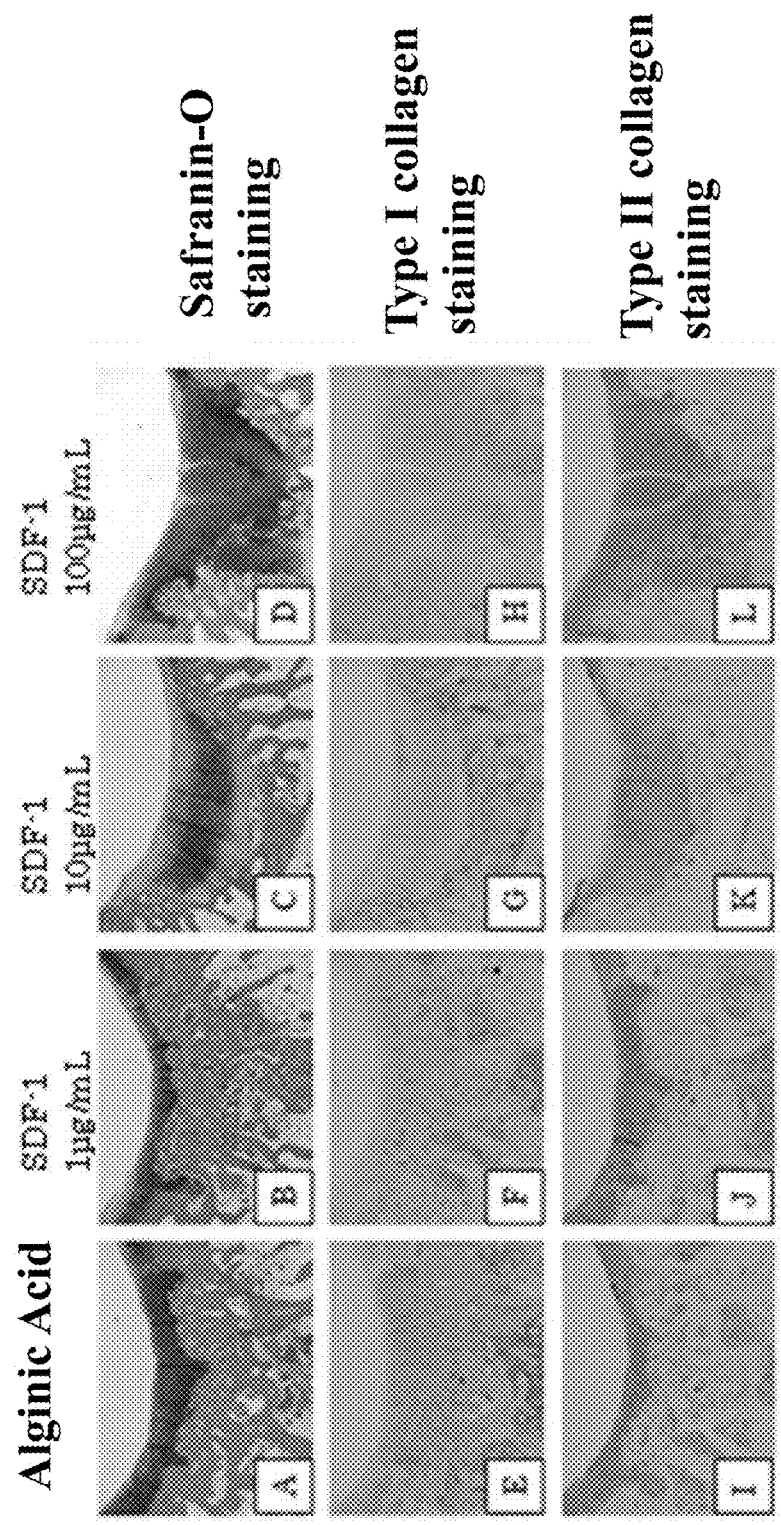
Fig. 6A-L

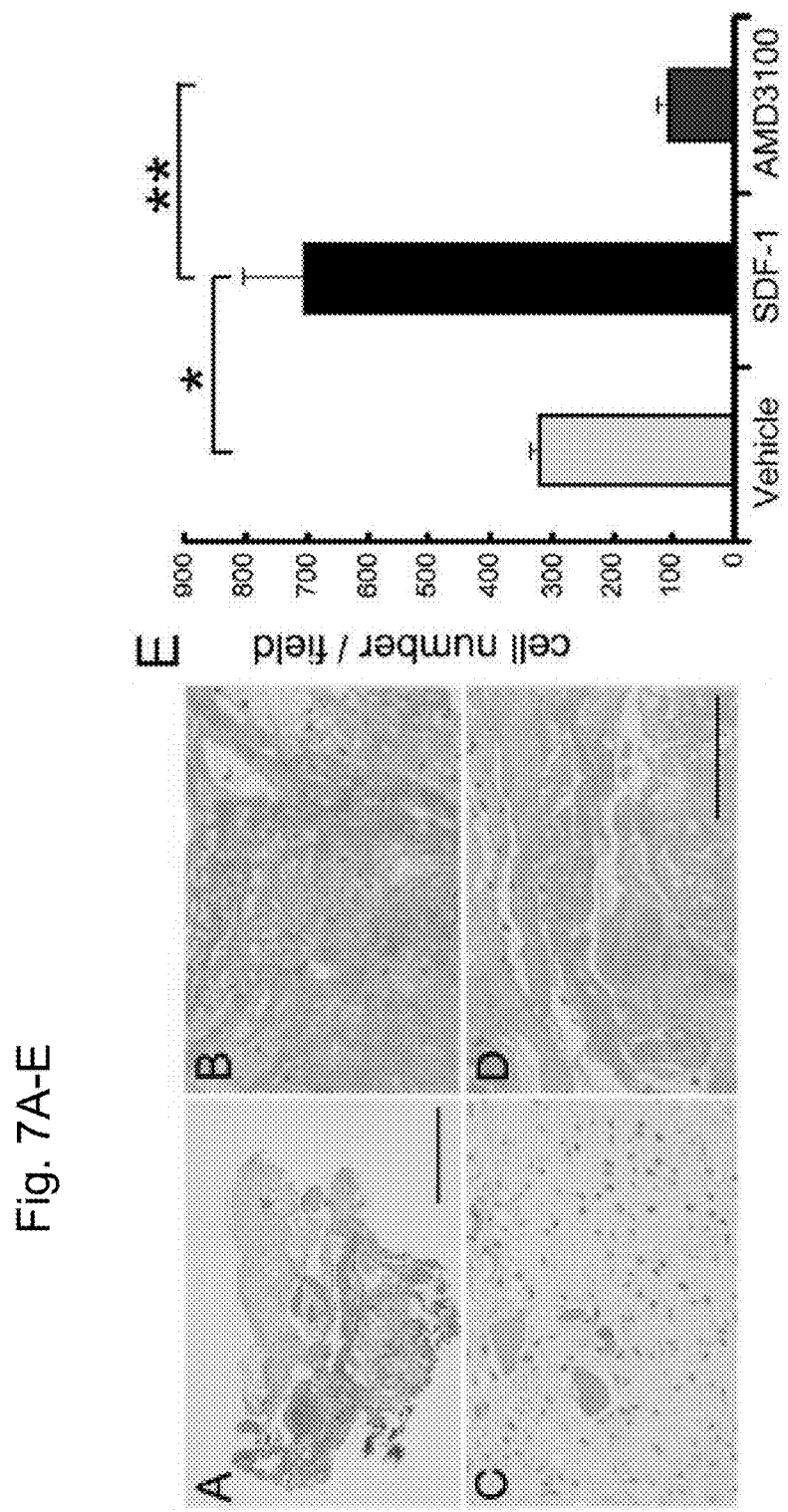
Fig. 7A-E

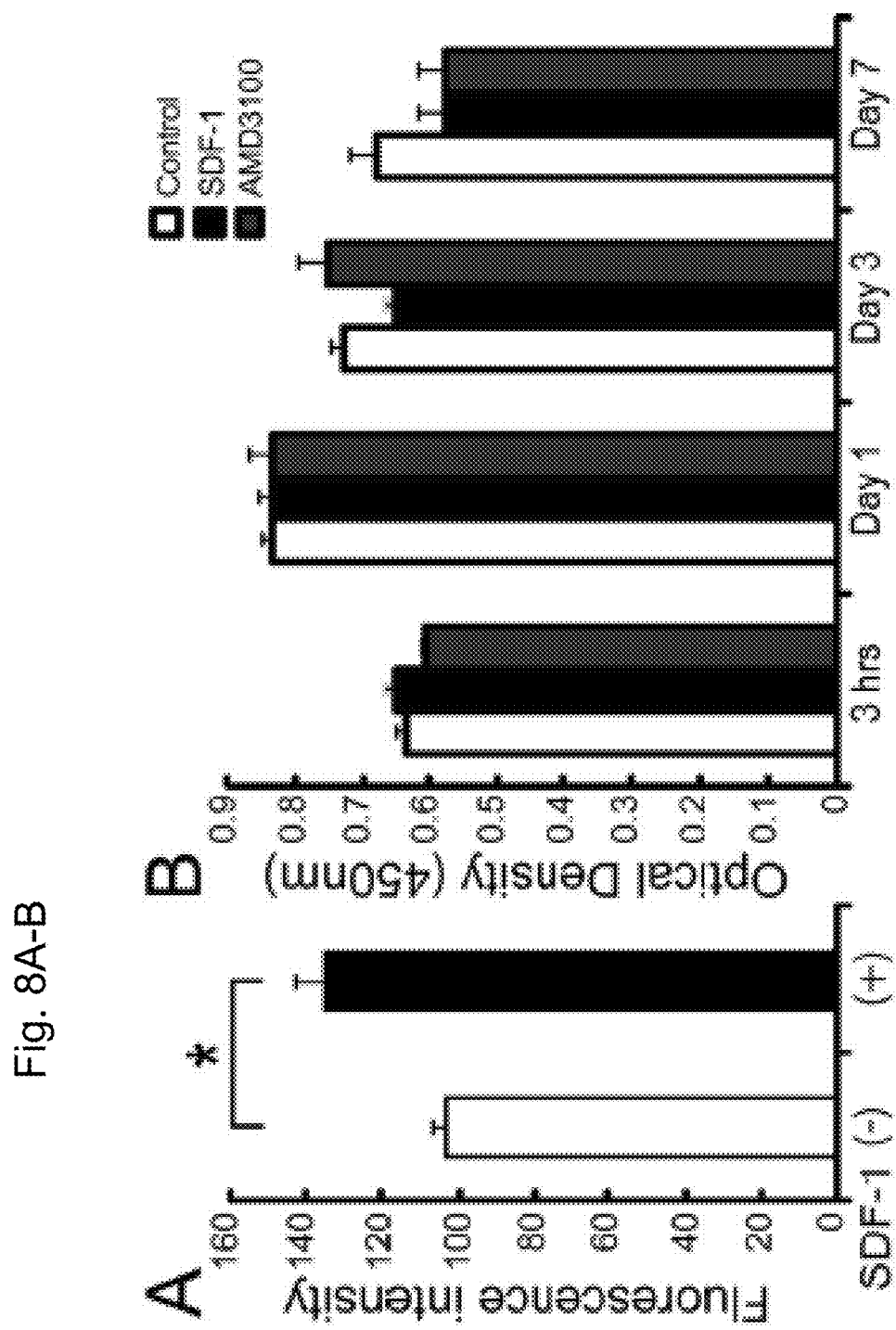
Fig. 8A-B

METHOD FOR REGENERATING CARTILAGE COMPRISING APPLYING A MONOVALENT METAL SALT OF ALGINIC ACID AND SDF-1

CROSS-REFERENCE TO RELATED APPLICATIONS

This application is a Continuation of U.S. application Ser. No. 14/239,663, now abandoned, which is the U.S. National Stage application of PCT/2012/071749, filed Aug. 22, 2012, which claims priority from Japanese application JP 2011-181662, filed Aug. 23, 2011.

TECHNICAL FIELD

The present invention relates to a composition for cartilage regeneration and the like.

BACKGROUND ART

Articular cartilage is hyaline cartridge that is composed of a small number of cells, collagenous extracellular matrix, abundant proteoglycans and water. Since vascular and neural networks are present in the bone and the bone has self-repairing ability, even when a bone is fractured, the fractured site is often adequately repaired. Articular cartilage, however, lacks vascular and neural networks. Accordingly, it has very little self-repairing ability and thus a cartilage defect lesion is not adequately repaired particularly when a large defect lesion is formed in the cartilage. Even when the lesion is repaired, the lesion is remodeled with fibrous cartilage that has different mechanical property from that of hyaline cartilage. Therefore, a cartilage defect lesion leads to pain in the joint and loss of joint function, which often result in development of osteoarthritis. In addition, an early stage of osteoarthritis, where abrasion of the surface of articular cartilage starts due to aging or excessive joint usage, may lead to cartilage defect over a large region as a result of progression of the symptoms.

Thus, since articular cartilage is inadequate in self-repairing ability, surgical procedures for treating cartilage lesion, for example, autologous osteochondral implantation (mosaicplasty), a procedure of perforating with a pick (microfracture), drilling, a procedure of shaving subchondral bone with a burr (abrasion procedure) and resection of injured cartilage (debridement) are required. Among these procedures, the microfracture procedure, drilling and the abrasion procedure are called marrow stimulation techniques, which stimulate bleeding from bone marrow to induce marrow-derived cartilage precursor cells in expectation of them to differentiate into cartilage. These techniques, however, have limitation for a widespread cartilage defect and cartilage regenerated by these procedures is fibrous cartilage that has different mechanical property from that of hyaline cartilage.

In 1984, Peterson et al. and Grande et al. tested autologous chondrocyte implantation (ACI) technique in the non-full thickness of rabbit articular cartilage. ACI is a technique involving harvesting and culturing tissue from patient's own normal cartilage, implanting the cultured cells suspended in a medium in the affected area and covering the cartilage defect lesion with a piece of periosteum to prevent leakage of the cells. ACI technique was first clinically applied in 1994 and now has been used for more than 15 years. Until now, several clinically successful examples have been reported. Recent clinical examinations, however, also report that ACI technique did not show significantly superior results over other surgeries with respect to repair of an articular cartilage defect.

There are two major reasons for such poor results from the ACI technique. One reason is the technical difficulties in anchoring cells and a scaffold to the joint defect lesion and covering them with a periosteum patch. In ACI technique, the joint needs to be widely exposed by arthrotomy to suture the periosteum patch to cover the cell suspension. Moreover, several complicated issues related to the periosteum patch including thickening, defect and intra-articular adhesion of periosteum have also been reported. The other reason is the limitation to the use of chondrocytes. Chondrocytes rapidly lose their differentiation phenotypes in monolayer culture and transform into fibroblasts. Another problem is that harvest of cartilage from a non-weight-bearing site of the affected joint required by the ACI technique leaves the problem of the donor site that has been harvested of chondrocytes to remain problematic.

Meanwhile, there has been an attempt to utilize natural polymers such as collagen, chitosan, agarose and alginic acid in regenerative medicine for articular cartilage. It is, however, difficult to acquire sufficient cartilage regeneration effect with polymer alone, and polymer is usually used in combination with cultured chondrocytes and mesenchymal stem cells. For example, Patent Document 1 discloses that mesenchymal stem cells embedded in a composition containing a monovalent metal salt of a low endotoxin alginic acid can be applied to a cartilage injury lesion to gain favorable hyaline cartilage regeneration that is almost comparable to normal cartilage. In addition, an attempt to use growth factors and cytokines has also been made in cartilage regeneration medicine. TGF-β and bFGF are known as typical factors for differentiating/proliferating chondrocytes.

SDF-1 (Stromal cell-derived factor 1) is one type of chemokines. SDF-1 is expressed in ischemic tissues caused by cardiac infarction, brain infarction, and skin lesion and the like to allow the vascular precursor cells to migrate toward the ischemic site for angiogenesis. Non-patent Document 1 describes that SDF-1 expression was confirmed in the bone implantation site and that SDF-1 played a role in guiding mesenchymal stem cells to the local site upon bone healing. Patent Document 2 discloses a sustained-release composition comprising SDF-1 and a hydrogel of modified gelatin. This composition is utilized for the treatment of ischemic diseases and the like because it allows sustained release of SDF-1. On the other hand, whether or not SDF-1 is expressed at the cartilage injury lesion and whether or not it exerts a beneficial effect upon administration to the cartilage injury lesion have previously been unknown. There is also a report saying that SDF-1 is present at a higher concentration in a pathological tissue of osteoarthritis or rheumatoid arthritis than in a normal tissue, and that SDF-1 of a higher concentration (200 ng/ml or higher, which is less than 100 ng/ml in a normal tissue) can result in necrosis of chondrocytes (Non-patent Document 2).

Patent Document 3 discloses a cell-free graft comprising an open porous structuring matrix and a serum. This cell-free graft is described of its potential to be used for cartilage regeneration since the serum in the graft can stimulate migration of mesenchymal precursor cells to the defect lesion, but whether or not it actually exerts a cartilage regeneration effect in vivo remains unrevealed. Generally, in cartilage regeneration medicine, it is difficult to predict the in vivo effect of implantation therapy only by in vitro cartilage regeneration tests or cell migration tests. Specifically, a graft used in cartilage regeneration medicine needs to provide performances, for example, to remain at the injury lesion for weeks, to successfully graft with the surrounding tissue as regenerated cartilage and the like. It is difficult to confirm such performances other than in vivo.

Patent Document 4 describes that a cell-free scaffold containing SDF-1 or TGF-β is arranged in a manner to allow fluid communication with cells, thereby rending the cells to migrate toward the scaffold. The scaffold actually used in Patent Document 4 is collagen sponge covered with cross-linked calcium alginate. Gelatin microspheres containing SDF-1 and/or TGF-β are embedded in the cross-linked calcium alginate layer of the scaffold. Patent Document 4 reports that when this scaffold was brought into contact with bone-marrow-derived mesenchymal stem cells (MSC), human adipose-derived stem cells (ASC) and synovial stem cells (SYN), with the collagen sponge side facing down, the cells in some cases had migrated to the collagen sponge of the scaffold. It also describes that although cartilage formation was confirmed with the scaffold containing TGF-β, the cell migration thereof was moderate, whereas the scaffold containing both TGF-β and SDF-1 resulted in good cell migration and cartilage formation were confirmed. Patent Document 4, however, does not show that the cells migrate to the cross-linked calcium alginate layer of the scaffold. Patent Document 4 also concludes that although MSC and ASC migrated to the scaffold containing only SDF-1 and not TGF-β, it was inadequate to induce cartilage formation with SDF-1 alone.

PRIOR ART DOCUMENTS

Patent Documents

[Patent Document 1] WO2008/102855 (pamphlet)
[Patent Document 2] WO2009/060608 (pamphlet)
[Patent Document 3] WO2007/003324 (pamphlet)
[Patent Document 4] WO2010/048418 (pamphlet)

Non-Patent Documents

[Non-patent Document 1] Toshiyuki Kitaori et al., The Journal of Clinical Orthopaedic Association, Vol. 45, No. 1, pp. 72-75 (2010)
[Non-patent Document 2] Lei Wei et al., The Journal of Rheumatology, Vol. 33, pp. 1818-1826 (2006)

DISCLOSURE OF INVENTION

Under the above-described circumstances, there has been a need in the cartilage regeneration medicine for a composition for cartilage regeneration, which can reduce the burden on patients such as cell harvest, arthrotomy and the like, which can easily be applied to a cartilage injury lesion, and which can exert a cartilage regeneration effect in vivo. In particular, a novel composition for cartilage regeneration has been expected that can produce a good hyaline cartilage regeneration effect that resembles that of normal cartilage without using graft cells.

In order to solve the above-described problems, the present inventors have gone through intensive studies and found that good cartilage regeneration can be induced at a cartilage injury lesion without using graft cells by applying to the cartilage injury lesion a composition for cartilage regeneration wherein (a) a monovalent metal salt of a low endotoxin alginic acid and (b) SDF-1 are used in combination, thereby accomplishing the present invention.

Thus, the present invention provides a composition for cartilage regeneration as follows.

[1-1] A composition for cartilage regeneration wherein (a) a monovalent metal salt of a low endotoxin alginic acid and (b) SDF-1 are used in combination.
[1-2] The composition according to [1-1] above, wherein the composition does not contain a cell growth factor.
[1-3] The composition according to either one of [1-1] and [1-2], wherein the SDF-1 is contained in the composition at a concentration of 0.2 μg/ml or higher and less than 100 μg/ml.
[1-4] The composition according to any one of [1-1] to [1-3] above, wherein the composition is applied to a cartilage injury lesion, and is cured by applying a cross-linking agent to the surface of the composition.
[1-5] The composition according to [1-4] above, wherein the cross-linking agent is at least one metal ion compound selected from the group consisting of $Ca^{2+}$, $Mg^{2+}$, $Ba^{2+}$ and $Sr^{2+}$.
[1-6] The composition according to any one of [1-1] to [1-5] above, wherein the monovalent metal salt of alginic acid has a weight-average molecular weight of 500,000 or more in gel filtration chromatography.
[1-7] The composition according to any one of [1-1] to [1-6] above, wherein viscosity of the composition is 400 mPa·s to 20,000 mPa·s.
[1-8] The composition according to any one of [1-1] to [1-7] above, wherein the composition does not contain cells for cartilage regeneration.
[1-9] The composition according to any one of [1-1] to [1-8] above, wherein the composition does not contain a scaffold material for cells except (a) the monovalent metal salt of low endotoxin alginic acid.
[1-10] The composition according to any one of [1-1] to [1-9] above, wherein the monovalent metal salt of alginic acid is potassium alginate or sodium alginate.
[1-11] The composition according to any one of [1-1] to [1-10] above, wherein the monovalent metal salt of low endotoxin alginic acid has an endotoxin content of 100 EU/g or less.
[1-12] The composition according to any one of [1-1] to [1-11] above, wherein the composition for cartilage regeneration is used for treating a cartilage injury lesion or for treating a cartilage disease.

In addition, the present invention also provides a method of regenerating cartilage as follows.

[2-1] A method for regenerating cartilage comprising the step of applying to a cartilage injury lesion a composition wherein (a) a monovalent metal salt of low endotoxin alginic acid and (b) SDF-1 are used in combination.
[2-2] The method according to [2-1] above, wherein the composition does not contain a cell growth factor.
[2-3] The method according to either one of [2-1] and [2-2], wherein the concentration of SDF-1 in the composition is 0.2 μg/ml or higher and less than 100 μg/ml.
[2-4] The method according to any one of [2-1] to [2-3] above, wherein the composition is applied to the cartilage injury lesion, and is cured by applying a cross-linking agent to the surface of the composition.
[2-5] The method according to [2-4] above, wherein the cross-linking agent is at least one metal ion compound selected from the group consisting of $Ca^{2+}$, $Mg^{2+}$, $Ba^{2+}$ and $Sr^{2+}$.
[2-6] The method according to any one of [2-1] to [2-5] above, wherein the monovalent metal salt of alginic acid has a weight-average molecular weight of 500,000 in gel filtration chromatography.

[2-7] The method according to any one of [2-1] to [2-6] above, wherein viscosity of the composition is 400 mPa·s to 20,000 mPa·s.

[2-8] The method according to any one of [2-1] to [2-7] above, wherein the composition does not contain cells for cartilage regeneration.

[2-9] The method according to any one of [2-1] to [2-8] above, wherein the composition does not contain a cell scaffold material for cells except (a) the monovalent metal salt of low endotoxin alginic acid.

[2-10] The method according to any one of [2-1] to [2-9] above, wherein the monovalent metal salt of alginic acid is potassium alginate or sodium alginate.

[2-11] The method according to any one of [2-1] to [2-10] above, wherein the monovalent metal salt of low endotoxin alginic acid has an endotoxin content of 100 EU/g or less.

[2-12] The method according to any one of [2-1] to [2-11] above, wherein the method is used for treating a cartilage injury lesion or for treating a cartilage disease.

The present invention provides a composition for cartilage regeneration in cartilage regeneration medicine, which can reduce the burden on patients such as cell harvest, arthrotomy and the like, which can easily be applied to a cartilage injury lesion, and which can exert cartilage regeneration effect in vivo. A composition for cartilage regeneration according to a preferred embodiment of the present invention is capable of inducing hyaline cartilage regeneration that resembles that of normal cartilage without using graft cells.

BRIEF DESCRIPTION OF THE DRAWINGS

FIGS. 1A-J show expression of SDF-1 protein in rabbit osteochondral defect models in Example 1. (A-D) are SDF-1 immunohistostaining images at cartilage injury lesions at predetermined time points following the procedure of creating full-thickness osteochondral defect. The black arrow indicates a cell that is expressing SDF-1 protein. (E-H) are SDF-1 immunohistostaining images at intact joint surfaces of a sham surgery group at predetermined time points. The scale bar is 50 µm. (I) is a low magnification image of a cartilage injury lesion following a week after the procedure. The scale bar is 1 mm. (J) shows Western blots. "Sham" represents the sham surgery group and "Defect" represents the full-thickness osteochondral defect created group.

FIGS. 2A-J show images showing macroscopic findings at Week 4 (A-D) and macroscopic findings at Week 16 (E-H) in rabbit osteochondral defect models in Example 2. "Defect" represents an untreated group, "Vehicle" represents an alginic acid group, "SDF-1" represents an alginic acid+SDF-1 administration group, and "AMD3100" represents an alginic acid+AMD3100 administration group. (I) shows macroscopic scores at Week 4 and (J) shows macroscopic scores at Week 16 (n=10). *p<0.05, **p<0.01, †p<0.001

FIGS. 3A-M show images of histological sections of the rabbit osteochondral defect models of Example 2 at Week 4. "Defect" represents the untreated group, "Vehicle" represents the alginic acid group, "SDF-1" represents the alginic acid+SDF-1 administration group, and "AMD3100" represents the alginic acid+AMD3100 administration group. (A-D) are results from safranin-O staining, (E-H) are results from staining with an anti-type I collagen antibody, and (I-L) are results from staining with an anti-type II collagen antibody. The scale bar is 500 µm. (M) shows histological scores at Week 4 (n=5). *p<0.01, **p<0.001

FIGS. 4A-M show images of histological sections of the rabbit osteochondral defect model of Example 2 at Week 16. "Defect" represents the untreated group, "vehicle" represents the alginic acid group, "SDF-1" represents the alginic acid+SDF-1 administration group, and "AMD3100" represents the alginic acid+AMD3100 administration group. (A-D) are results from safranin-O staining, (E-H) are results from staining with an anti-type I collagen antibody, and (I-L) are results from staining with an anti-type II collagen antibody. The scale bar is 500 µm. (M) shows histological scores at Week 16 (n=5). *p<0.01, **p<0.001

FIGS. 5A-H show images showing macroscopic findings at Week 4 (A-D) and macroscopic findings at Week 12 (E-H) with respect to "(2-5) Assessment of SDF-1 dosage" in Example 2.

FIGS. 6A-L show histological sections at Week 12 with respect to "(2-5) Assessment of SDF-1 dosage" in Example 2. (A-D) are results from safranin-O staining, (E-H) are results from staining with an anti-type I collagen antibody, and (I-L) are results from staining with an anti-type II collagen antibody.

FIGS. 7A-E show images of H-E staining of implanted alginic acid gel for assessing in vivo cell homing in Example 3. (A-D) show sample sections following a week after the surgery. (A) is a low magnification image with a scale bar of 1 mm. (B-D) shows high magnification images with a scale bar of 100 µm. (B) shows an alginic acid group, (C) shows an alginic acid+SDF-1 administration group and (D) shows an alginic acid+AMD3100 administration group. (E) shows the cell counts within the fields (n=5). *p<0.01, **p<0.001

FIGS. 8A-B show the results from the in vitro assessment of the effect of SDF-1 on the behavior of BMSC in Example 4. (A) shows the results from the cell migration test using CytoSelect™ in media with or without SDF-1. The vertical axis represents fluorescence intensity that reflects the cell counts (n=16). (B) shows the results from the cell proliferation test. The vertical axis represents absorbance that reflects the cell counts (n=5).

BEST MODES FOR CARRYING OUT THE INVENTION

Hereinafter, the present invention will be described in detail. The following embodiments, however, are examples for illustrating the present invention, and the present invention may be carried out in various embodiments without departing from the scope of the invention.

1. Cartilage Regeneration

"Cartilage" is found in joints, thoracic walls, intervertebral discs, meniscus, and in tubular structures such as larynx, respiratory tract and ears, and can be classified into three types, namely, hyaline cartilage, elastic cartilage and fibrous cartilage. For example, articular cartilage is hyaline cartilage which is composed of chondrocytes, collagenous extracellular matrix, proteoglycans and water and which is free of vascular distribution. Hyaline cartilage is characteristic in that it is abundant in type II collagen that is stained with an anti-type II collagen antibody, and it is stained red upon safranin-O staining that stains proteoglycans.

"Cartilage injury" refers to states where the cartilage has been injured due to aging, traumatic injury or other various factors, including states with deteriorated cartilage functions, for example, a state where viscoelasticity unique to cartilage (meaning that the cartilage is slowly compressed with a load and slowly returns to its original state once released from the load) is decreased for some reason so that the ability of the cartilage to support a load while retaining the mobility thereof is interfered. The cartilage injuries can also be seen in diseases such as osteoarthritis and rheumatoid arthritis. The present invention relates to a composition for cartilage regeneration which can be applied to such cartilage injury lesion. Cartilage defect refers to a site that lacks a cartilage layer, including a cavity in the cartilage tissues and the surrounding tissues that form said cavity. Cartilage defect is one aspect of cartilage injury, and a composition of the present invention can favorably be used for treating a cartilage defect lesion.

More particularly, a composition of the present invention is a composition for cartilage regeneration wherein (a) a monovalent metal salt of low endotoxin alginic acid and (b) SDF-1 are used in combination. By using the composition of the present invention, better cartilage can be regenerated as compared to the case where a monovalent metal salt of alginic acid is used alone. Since the composition of the present invention has good adhesive property to a cartilage injury lesion and can be applied with a syringe or the like, it can easily be applied to a cartilage injury lesion. It can be administered under an arthroscope when extensive arthrotomy can be avoided. A composition of a preferable embodiment of the present invention can induce good hyaline cartilage regeneration that resembles normal cartilage without using graft cells.

According to the present invention, "cartilage regeneration" or "cartilage tissue regeneration" means to regenerate the function of cartilage at a cartilage injury lesion with functional disorder or dysfunction. According to the present invention, regeneration of the function does not have to be complete regeneration of the function as long as the function is recovered compared to the state of the cartilage injury lesion before application of the composition of the present invention. Provided that the state of normal cartilage before receiving injury is 100% and that the state of a cartilage injury lesion prior to application of the composition of the present invention is 0%, the state is preferably recovered to 30% or higher, more preferably 50% or higher, more preferably 80% or more and particularly preferably almost to the state before the injury. A rate of occurrence of cartilage other than hyaline cartilage, such as fibrous cartilage, is preferably low during the cartilage regeneration. Moreover, the phrase "treatment of a cartilage injury lesion" or "treatment of a cartilage defect lesion" means that the cartilage at the cartilage injury lesion or the cartilage defect lesion found in aging, traumatic injury, osteoarthritis, intervertebral disc damage, meniscus damage, osteochondral dissecans or the like is regenerated so as to alleviate or heal these conditions. Furthermore, the phrase "treatment of a cartilage disease" means that cartilage at a cartilage injury lesion or a cartilage defect lesion found in the cartilage disease such as osteoarthritis, rheumatoid arthritis or neurogenic arthropathy is regenerated so as to alleviate or heal these conditions. One embodiment of a composition for cartilage regeneration of the present invention is a composition for regenerating hyaline cartilage. Hyaline cartilage regeneration has a purpose of regenerating cartilage in which the proportion of the hyaline cartilage is higher than that of the fibrous cartilage, and intends to regenerate cartilage tissues that are abundant in type II collagen and proteoglycans.

In addition, the phrase "application to a cartilage injury lesion" means to bring the composition for cartilage regeneration to make contact with a cartilage injury lesion, where a composition of the present invention is preferably injected into a cartilage defect lesion so as to fill in the defect lesion. Alternatively, one or more relatively small holes may be formed into a cartilage injury lesion, preferably a cartilage defect lesion, so as to inject the composition of the present invention to fill in the holes. Application to a cartilage injury lesion is preferably injection that sufficiently fills the cavity volume of the affected area. The affected area is preferably subjected to a necessary pretreatment, and if necessary, washed, prior to the application of the composition of the present invention. The phrase "to wash an affected area" means to remove blood components, other unwanted tissues and the like from a site that is to be applied with the composition of the present invention, for example, with physiological saline or the like. At the end of washing, the affected area is preferably dried, for example, by wiping off the remaining unwanted fluid components before applying the composition of the present invention.

2. Monovalent Metal Salt of Alginic Acid

A "monovalent metal salt of alginic acid" contained in a composition for cartilage regeneration of the present invention is a water-soluble salt that is formed through ion exchange between a hydrogen atom of carboxylic acid at position 6 of alginic acid and a monovalent metal ion such as $Na^+$ or $K^+$. Specific examples of monovalent metal salts of alginic acid include sodium alginate and potassium alginate, while sodium alginate that can be obtained as a commercially available product is particularly preferable. A solution of a monovalent metal salt of alginic acid forms a gel when mixed with a cross-linking agent.

An "alginic acid" used in the present invention is a biodegradable polymeric polysaccharide, which is a polymer resulting from linear polymerization of two types of uronic acids called D-mannuronic acid (M) and L-guluronic acid (G). More specifically, alginic acid is a block copolymer which has a homopolymer fraction of D-mannuronic acid (MM fraction), a homopolymer fraction of L-guluronic acid (GG fraction) and a fraction having randomly arranged D-mannuronic acids and L-guluronic acids (MG fraction), arbitrarily linked together. A composite ratio of D-mannuronic acid to L-guluronic acid (M/G ratio) of alginic acid varies primarily according to the type of a biological origin thereof such as seaweed, and is affected by the habitat and seasons of said biological origin. The M/G ratio widely ranges from about 0.4 that is rich in G to about 5 that is rich in M.

Since a monovalent metal salt of alginic acid is a polymeric polysaccharide, it is difficult to accurately determine the molecular weight thereof but in general its weight-average molecular weight is in a range of 10,000 to 10,000,000, and preferably 50,000 to 3,000,000. Since a lower molecular weight results in a poor cartilage regeneration effect, particularly in a poor hyaline cartilage regeneration effect, at a cartilage injury lesion, a monovalent metal salt of alginic acid used in the present invention preferably has a weight-average molecular weight of 500,000 or more.

In general, calculation of a molecular weight of a polymeric polysaccharide by gel filtration chromatography may result in 10 to 20% measurement error. For example, a value of 400,000 may vary within a range of 320,000 to 480,000, 500,000 may vary within a range of 400,000 to 600,000, and 1,000,000 may vary within a range of 800,000 to 12,000,000. Therefore, a preferable range of a weight-average molecular weight of a monovalent metal salt of alginic acid that is particularly favorable regarding an effect on cartilage is, at least 500,000 or more, more preferably 650,000 or more, and still more preferably 800,000 or more. Since an excessively high molecular weight is difficult to be produced and causes problems such as excessively high viscosity upon making an aqueous solution thereof and decreased solubility, the weight-average molecular weight is preferably 5,000,000 or less and more preferably 3,000,000 or less.

In general, since a polymeric substance derived from a natural origin do not have a single molecular weight but rather consists of an aggregate of molecules of various molecular weights, they are measured in a molecular weight distribution that has a certain range. A typical measurement method is gel filtration chromatography. Typical examples of information of a molecular weight distribution acquired by gel filtration chromatography include weight-average molecular weight (Mw), number-average molecular weight (Mn) and variance ratio (Mw/Mn).

A weight-average molecular weight places emphasis on the contribution of a polymer having a larger molecular weight to an average molecular weight, and is represented by the following formula:

$$Mw=\Sigma(WiMi)/W=\Sigma(HiMi)/\Sigma(Hi)$$

A number-average molecular weight is calculated by dividing the total weight of the polymers by the total number of the polymers:

$$Mn=W/\Sigma Ni=\Sigma(MiNi)/\Sigma Ni=\Sigma(Hi)/\Sigma(Hi/Mi)$$

Here, W represents the total weight of the polymers, Wi represents the weight of the "i"th polymer, Mi represents the molecular weight at the "i"th elusion time, Ni represents the number of molecular weights Mi, and Hi represents the height at the "i"th elusion time.

Since it is considered that a cartilage regeneration effect (particularly, a hyaline cartilage regeneration effect) at a cartilage injury lesion largely owes to molecular species with a larger molecular weight, a weight-average molecular weight can be employed as an indicator of the molecular weight.

A molecular weight measurement of a naturally-occurring polymeric substance is known to make a difference in the resulting value according to the measurement method (examples for hyaluronic acids: Chikako YOMOTA et. al. Bull. Natl. Health Sci., Vol. 117, pp 135-139(1999), and Chikako YOMOTA et. al. Bull. Natl. Inst. Health Sci., Vol. 121, pp 30-33(2003)). Molecular weight measurements of alginate are described in a literature, including a method of calculating a molecular weight from intrinsic viscosity and a method of calculating a molecular weight by SEC-MALLS (Size Exclusion Chromatography with Multiple Angle Laser Light Scattering Detection) (ASTM F2064-00 (2006), published by ASTM International). This literature suggests, in order to measure a molecular weight by size exclusion chromatography (i.e., gel filtration chromatography), use of a multi-angle laser light scattering detector (MALLS) in combination with a calibration curve using pullulan as a standard substance (i.e., measurement by SEC-MALLS). There is also an example of using the molecular weight determined by SEC-MALLS as a standard value of alginate in a catalogue (FMC Biopolymer, PRONOVA™ sodium alginates catalogue).

Unless otherwise stated, a molecular weight of alginate specified herein is a weight-average molecular weight calculated by gel filtration chromatography.

Typical conditions for gel filtration chromatography include use of a calibration curve using pullulan as a standard substance. The molecular weight of pullulan as a standard substance is preferably at least 1,600,000, 788,000, 404,000, 212,000 or 112,000. In addition, an eluent (200 mM sodium nitrate solution), column conditions and the like can be specified. As the column conditions, at least one column with an exclusion limit molecular weight of 10,000,000 or more is preferably used with a polymethacrylate resin filler. A typical column is TSK gel GMPWxl (diameter 7.8 mm×300 mm) (Tosoh Corporation).

Although a monovalent metal salt of alginic acid that is initially extracted from a brown alga has a large molecular weight and high viscosity, the molecular weight becomes smaller and the viscosity becomes lower during the processes of heat drying, lyophilization, purification and the like. Accordingly, appropriate temperature management at each step in production allows production of monovalent metal salts of alginic acid having different molecular weights. Monovalent metal salts of alginic acid having larger molecular weights can be obtained by managing the temperature at each step in production to be lower whereas monovalent metal salts of alginic acid with smaller molecular weights can be obtained with higher temperature. Additionally, techniques such as appropriate selection of brown algae as the raw material or fractionation based on molecular weights during the production process can also allow production of monovalent metal salts of alginic acid having different molecular weights. Furthermore, after the molecular weight or the viscosity of the monovalent metal salt of alginic acid produced by a certain technique is measured, it can be mixed with a monovalent metal salt of alginic acid from other lot having different molecular weight or viscosity so as to obtain a monovalent metal salt of alginic acid having a molecular weight of interest.

Although alginic acid used in the present invention may either be naturally derived or synthesized, it is preferably naturally derived. Examples of naturally-occurring alginic acids include those extracted from brown algae. Although brown algae containing alginic acid grow in the coastal regions around the world, seaweeds that can actually be used as a raw material for alginic acid are limited with typical examples being *Lessonia* from South America, *Macrocystis* from North America, *Laminaria* and *Ascophyllum* from Europe, *Durvillea* from Australia and the like. Examples of brown algae that can serve as raw materials of alginic acids include *Lessoni* species, *Macrocystis* species, *Laminaria* species, *Ascophyllum* species, *Durvillea* species, *Eisenia* species and *Ecklonia* species.

Preferably, the content of the monovalent metal salt of alginic acid in the composition for cartilage regeneration of the present invention is about 0.5 to 10% w/v.

The monovalent metal salt of alginic acid in the composition for cartilage regeneration of the present invention is an active element that exerts an effect by providing environment suitable for cells that contribute to cartilage regeneration, for example, host-derived mesenchymal stem cells that have migrated to the affected area, to differentiate into chondrocytes, and the chondrocytes to regenerate cartilage.

3. Low Endotoxin Treatment

The monovalent metal salt of alginic acid contained in the composition for cartilage regeneration of the present invention is a monovalent metal salt of low endotoxin alginic acid. Low endotoxin means that the level of endotoxin is lowered to an extent that does not raise substantial inflammation or fever. Specifically, the alginic acid has been subjected to a low endotoxin treatment. By using a low endotoxin alginic acid in a composition of the present invention, a composition with high bioaffinity can be obtained, which causes less degeneration and low inflammation response in the surrounding cartilage.

The low endotoxin treatment can be performed according to a known method or a method pursuant thereto. For example, the treatment can be carried out according to the method of Suga et al. involving purification of sodium hyaluronate (see, for example, Japanese Unexamined Patent Application Publication No. Heisei 9-324001), the method of Yoshida et al., involving purification of β1,3-glucan (see, for example, Japanese Unexamined Patent Application Publication No. Heisei 8-269102), the method of William et al. involving purification of a biopolymer salt such as alginate or gellan gum (see, for example, Japanese Unexamined Patent Application Publication (Translation of PCT Publication) No. 2002-530440), the method of James et al. involving purification of a polysaccharide (see, for example, International Publication No. 93/13136), the method of Lewis et al. (see, for example, specification of U.S. Pat. No. 5,589,591), the method of Hermanfranck et al. involving purification of alginate (see, for example, Appl Microbiol Biotechnol (1994) 40:638-643) or methods pursuant thereto. The low endotoxin treatment of the present invention is not limited thereto, and can be carried out by a known method such as washing, filtration with a filter (such as an endotoxin-removing filter or an electrically-charged filter), ultrafiltration, purification with a column (such as an endotoxin adsorption affinity column, a gel filtration column or an ion-exchange resin column), adsorption to a hydrophobic substance, a resin or activated charcoal, a treatment with an organic solvent (extraction with an organic solvent, deposition/precipitation through addition of an organic solvent, or the like), a surfactant treatment (see, for example, Japanese Unexamined Patent Application Publication No. 2005-036036), or an appropriate combination thereof. The steps in these treatments may appropriately be combined with a known method such as centrifugation. Preferably, the treatment is suitably selected according to the type of the alginic acid.

An endotoxin level can be confirmed and measured according to a known method such as a method using a limulus agent (LAL), or a method using Endospecy (registered trademark) ES-24S set (Seikagaku Corporation). Although a method for treating endotoxin of an alginic acid contained in the composition of the present invention is not particularly limited, the resulting endotoxin content of a monovalent metal salt of alginic acid is preferably 500 endotoxin unit (EU)/g or less, more preferably 100 EU/g or less, still more preferably 50 EU/g or less, and particularly 30 EU/g or less upon endotoxin measurement using a limulus agent (LAL). Sodium alginate that has been subjected to a low endotoxin treatment is available, for example, as a commercially available product such as Sea Matrix (sterilized) (Kimika Corporation-Mochida International Ltd.) and PRONOVA™ UP LVG (FMC).

4. SDF-1

A composition for cartilage regeneration of the present invention is characterized in that SDF-1 is used in combination with the monovalent metal salt of low endotoxin alginic acid.

SDF-1 according to the present invention is capable of exerting an improved cartilage regeneration effect by being added to an alginic acid, as compared to the effect of the alginic acid alone. In the composition for cartilage regeneration of the present invention, SDF-1 is an active element that exerts an effect of promoting migration of host-derived cells (e.g., cells that contribute to cartilage regeneration, such as mesenchymal stem cells) to the affected area.

SDF-1 (Stromal cell-derived factor 1) is a protein that is also called CXCL-12 or PBSF, and belongs to the CXC chemokine family having four conserved cysteine residues.

SDF-1 used in the present invention may be derived from human or a non-human mammal such as bovine, monkey, cat, mouse, rat, guinea pig, hamster, pig, dog, rabbit, sheep or horse. Preferably, SDF-1 is derived from human.

Isoforms of human SDF-1 have been confirmed to exist, such as SDF-1α (Genbank registration number NP_954637), SDF-1β (Genbank registration number NP_000600), SDF-1γ (Genbank registration number NP_001029058) and SDF-1δ (Genbank registration number NP_001171605). SDF-1α is a peptide of 89 a.a. The sequence of 1-88 a.a. of SDF-1α is conserved among the isoforms, where β, γ and δ have addition of +5 a.a., +31 a.a. and +52 a.a. at the C-terminal side, respectively. Moreover, 1-21 a.a. of SDF-1α at the N-terminal side is cleaved upon becoming a mature peptide. Thus, 22-88 a.a. of SDF-1α is considered as the minimum active unit, and any peptide can be used as SDF-1 as long as it has this unit. Preferably, SDF-1 used in the present invention is human mature SDF-1α or human mature SDF-1β.

SDF-1 used in the present invention may have one or more amino acids in its amino acid sequence substituted, inserted, deleted and/or added, and/or may have a sugar chain substituted, deleted and/or added, as long as it has an activity as a chemokine. Amino acid mutation is accepted as long as SDF-1 retains at least four cysteine residues (Cys30, Cys32, Cys55 and Cys71 in the case of human SDF-1α) and as long as it has identity in a range of 90% or more to the original natural amino acid sequence. Alternatively, it may be provided in a form of a physiologically-accepted salt. While salts with physiologically-accepted bases (e.g., alkali metals, etc.) or acids (organic and inorganic acids) can be used as "physiologically-accepted salts", physiologically-accepted acid addition salts are particularly favorable. Examples of such salts include salts with inorganic acids (for example, hydrochloric acid, phosphoric acid, hydrobromic acid and sulfuric acid) and salts with organic acids (for example, acetic acid, formic acid, propionic acid, fumaric acid, maleic acid, succinic acid, tartaric acid, citric acid, malic acid, oxalic acid, benzoic acid, methanesulfonic acid and benzenesulfonic acid).

SDF-1 used in the present invention may readily be prepared according to a known technique or otherwise available as a commercially available product. In the case where SDF-1 is to be prepared, for example, it may be prepared as a recombinant SDF-1 by a genetic engineering procedure or may be prepared by a peptide synthesis procedure. In the case where SDF-1 is to be obtained as a commercially available product, for example, Recombinant Human/Rhesus Macaque/Feline CXCL12/SDF-1 alpha (#350-NS-050, R&D Systems Inc.), Recombinant Human/Rhesus Macaque/Feline CXCL12/SDF-1 beta (#351-FS-050, R&D Systems Inc.), Human SDF-1α(#130-096-137, Miltenyi Biotec Inc.) or the like can be used.

When SDF-1 is to be contained in a composition for cartilage regeneration of the present invention, it is added such that the SDF-1 content in the composition for cartilage regeneration of the present invention is preferably 0.2 μg/ml or more and less than 100 μg/ml and more preferably 1 μg/ml or more and less than 60 μg/ml.

5. Preparation of Composition for Cartilage Regeneration

A composition for cartilage regeneration of the present invention is characterized in that (a) a monovalent metal salt of low endotoxin alginic acid and (b) SDF-1 are used in combination. Hereinafter, (a) a monovalent metal salt of low endotoxin alginic acid may be referred to as "component (a)" and (b) SDF-1 as "component (b)".

According to the present invention, to "used in combination" refers to concomitant use, and means that it is acceptable as long as both components (a) and (b) are contained when the composition of the present invention is applied to a cartilage injury lesion and the form during the distribution process including sale does not particularly matter. For example, it may be provided either (1) in a form of a compounding agent that has both components (a) and (b) mixed and formulated together, or (2) in a form of two separately formulated formulations, i.e., components (a) and (b), provided in combination as a kit or provided separately, so as to be mixed and used upon application. In other words, SDF-1 as component (b) may be provided in a form of a compounding agent that is formulated by blending component (b) with component (a) in advance, or as a kit obtained by combining and packaging two types of separately formulated formulations, components (a) and (b).

Each or a mixture of components (a) and (b) may be provided in a solution state by using a solvent or provided as a solid material such as a lyophilization product. In this regard, even if the components are provided as solid materials, the composition of the present invention is made into a solution state with a solvent to have a fluidity upon administration.

The solvent is not particularly limited as long as it is biologically applicable, and examples include injectable water, purified water, distilled water, ion-exchanged water (or deionized water), Milli-Q water, physiological saline and phosphate buffered saline (PBS). Preferably, the solvent is injectable water, distilled water, physiological saline or the like.

In a composition for cartilage regeneration according to a preferable embodiment of the present invention, the content of the monovalent metal salt of alginic acid is about 0.5 to 10% w/v, and the content of SDF-1 is 0.2 µg/ml or more and less than 100 µg/ml in the composition.

For example, in order to provide a composition of 2% w/v alginic acid. 10 µg/ml SDF-1, an aqueous solution formulation already containing defined amounts of alginic acid and SDF-1 can be produced and provided as a compounding agent, or 1 mL of a 4% w/v aqueous alginic acid solution and 1 mL of 20 µg/ml aqueous SDF-1 solution can be included in a kit as separate formulations such that the whole amounts of them are mixed upon use to give a composition containing a final concentration of 2% w/v alginic acid. 10 µg/ml SDF-1.

6. Viscosity of Composition for Cartilage Regeneration

Although the viscosity of a composition for cartilage regeneration of the present invention is not particularly limited as long as the effect of the present invention can be obtained, it is preferably 400 mPa·s to 20,000 mPa·s. For example, it can be prepared to have an appropriate viscosity by using the above-described solvent or the like. Viscosity within such range gives good adhesive property to a cartilage injury lesion, and also allows injection into an articular cavity or a cartilage injury lesion with a syringe or the like. Moreover, when the composition for cartilage regeneration of the present invention has a viscosity of about 2,000 mPa·s or more, the adhesive property to a cartilage injury lesion is further improved. In particular, for example, in a case where a cartilage injury lesion of a human femoral joint surface is to be manipulated under an arthroscope, if the viscosity is about 5,000 mPa·s or more, the composition of the present invention can be injected into the cartilage defect lesion even if the open side of the cartilage defect lesion is facing down so that the composition of the present invention can be brought into contact with and attached to the cartilage injury surface for at least 1 minute without anchoring. If necessary, the surface of the composition can be anchored during the attachment. The adhesive property to the cartilage injury lesion can further be improved by increasing the viscosity. For example, when the viscosity is 10,000 mPa·s, the composition can be attached to the affected area without anchoring for a longer period of time as compared to the case where viscosity is 5,000 mPa·s. Therefore, when the opening of the cartilage defect lesion or the hole formed in the cartilage injury lesion or the cartilage defect lesion is inclined or facing down, the composition of the present invention is preferably attached to the injury lesion for at least 5 seconds, preferably 10 seconds or longer, more preferably 30 seconds or longer and particularly preferably 1 minute or longer without using anchoring means. By adjusting the viscosity, the composition of the present invention can ensure time for performing anchoring means on the surface of the composition. Here, "attached to the injury lesion" means that the composition of the present invention stays on the injury lesion without falling from the injury lesion. Accordingly, the composition of the present invention is advantageous in that the treatment can be conducted by a simple injection method even when the position of the site is difficult for the practitioner to treat, for example, the affected area is facing down, upon treatment, by adjusting the viscosity thereof.

Meanwhile, injection with a syringe or the like is easier when the viscosity is about 20,000 mPa·s or less. Injection with a syringe or the like is possible even when the viscosity is, for example, about 20,000 mPa·s, but when injection is difficult due to high viscosity, the composition of the present invention can be applied to the cartilage injury surface by using other means. In terms of easy manipulation with a syringe, the viscosity of the composition of the present invention is preferably 20,000 mPa·s or less, and more preferably 15,000 mPa·s or less. Thus, when the opening of the cartilage defect lesion or the hole formed in the cartilage injury lesion or the cartilage defect lesion is inclined or facing down, the viscosity of the composition of the present invention that is suitable for application to the cartilage injury lesion is preferably about 2,000 mPa·s or more in terms of adhesive property and 20,000 mPa·s or less in terms of easy handling of the composition. The viscosity is preferably 3,000 mPa·s to 15,000 mPa·s, more preferably 4,000 mPa·s to 10,000 mPa·s, and particularly preferably 5,000 mPa·s to 6,000 mPa·s.

The viscosity of the composition for cartilage regeneration can be adjusted by controlling, for example, the concentration of the alginic acid, the molecular weight of the alginic acid, the M/G ratio of the alginic acid or the like.

The viscosity of a solution of a monovalent metal salt of alginic acid becomes higher when the concentration of the alginic acid in the solution is high, and becomes lower when the concentration of the alginic acid in the solution is low. The viscosity becomes higher when the molecular weight of the alginic acid is large, and becomes lower when the molecular weight is small. For example, in order to obtain a viscosity of 400 mPa·s to 20000 mPa·s with an alginic acid having a molecular weight of about 1,700,000 Da (Sea Matrix), an aqueous alginic acid solution of about 1% w/v to 3% w/v may be used. When an alginic acid with a smaller molecular weight is used, the concentration of the alginic acid needs to be increased than the above case. The viscosity of the aqueous alginic acid solution can be measured according to a known method by using, for example, rotational viscometer (cone-plate type) (TVE-20LT, TOKI SANGYO CO., LTD., JAPAN) or the like.

Since the viscosity of a solution of a monovalent metal salt of alginic acid is affected by the M/G ratio, an alginic acid having a preferable M/G ratio can appropriately be selected, for example, according to the viscosity of the solution or the like. The M/G ratio of the alginic acid used in the present invention is about 0.4 to 4.0, preferably about 0.8 to 3.0, and more preferably about 1.0 to 1.6.

As previously described, since the M/G ratio is determined primarily by the type of the seaweed, the type of a brown alga used as the raw material has an effect on the viscosity of the solution of the monovalent metal salt of alginic acid. The alginic acid used in the present invention is preferably derived from a brown alga of *Lessonia* species, *Macrocystis* species, *Laminaria* species, *Ascophyllum* species or *Durvillea* species, more preferably derived from a brown alga of *Lessonia* species, and particularly preferably derived from *Lessonia nigrescens*.

7. Gelation of Surface of Composition

Some embodiments of the composition for cartilage regeneration of the present invention do not contain a cross-linking agent. When a composition for cartilage regeneration does not contain a cross-linking agent, the composition for cartilage regeneration containing a solution of a monovalent metal salt of alginic acid may be applied to a cartilage injury lesion and then a cross-linking agent may be applied to the surface of the composition. By gelating the surface of the composition to cure the surface, the composition can effectively be prevented from leaking from the cartilage injury lesion.

Such a cross-linking agent is not particularly limited as long as it can cross-link and anchor the surface of the solution of a monovalent metal salt of alginic acid, and examples include bivalent or higher metal ion compounds of $Ca^{2+}$, $Mg^{2+}$, $Ba^{2+}$ and $Sr^{2+}$, and cross-linking reagents that have two to four amino groups within their molecules. More specifically, examples of bivalent or higher metal ion compounds include $CaCl_2$, $MgCl_2$, $CaSO_4$, $BaCl_2$ and $SrCl_2$ (preferably, $CaCl_2$, $CaSO_4$, $BaCl_2$, etc.), while examples of cross-linking reagents having two to four amino groups within their molecules comprise diaminoalkanes optionally having a lysyl group on a nitrogen atom ($-COCH(NH_2)-(CH_2)_4-NH_2$), that is, diaminoalkane and derivatives thereof that form lysyl amino groups by substituting an amino group with a lysyl group, specific examples being diaminoethane, diaminopropane and N-(lysyl)-diaminoethane. In terms of easy access, gel strength and the like, the cross-linking agent is preferably a bivalent or higher metal ion compound of $Ca^{2+}$, $Mg^{2+}$, $Ba^{2+}$ or $Sr^{2+}$ (e.g., $CaCl_2$, $MgCl_2$, $CaSO_4$, $BaCl_2$, $SrCl_2$, etc.), more preferably $CaCl_2$, $CaSO_4$, $BaCl_2$ or the like, and particularly preferably a $CaCl_2$ solution.

A method for applying a bivalent or higher metal ion to the surface of the composition is not particularly limited, and an example includes a method in which a solution of a bivalent or higher metal ion is applied to the composition surface with a syringe, a spray or the like. The timing of applying the cross-linking agent to the surface of the composition of the present invention may be subsequent to or simultaneously with the application of the composition of the present invention to the defect lesion.

Preferably, a suitable amount of the cross-linking agent is suitably adjusted according to the size of the defect lesion to which the composition of the present invention has been applied. The cross-linking agent gradually penetrates inside from the surface of the composition, by which the cross-linking takes place. In order to prevent major impact by the cross-linking agent on the contact region between the composition of the present invention and the injury surface, the amount of the cross-linking agent applied is adjusted not to be excessive. The amount of the bivalent or higher metal ion applied is not particularly limited as long as it allows the surface of the composition containing the monovalent metal salt of alginic acid to be cured. When, for example, a 100 mM $CaCl_2$ solution is to be added, however, the amount added is preferably about 0.3 to 0.6 ml for a defect with a diameter of 5 mm and a depth of about 2 mm, and the dosage may be determined in proportion to the surface area of the affected area. For example, in the case of a defect with widths (10 mm×20 mm) and a depth of about 5 mm, the amount is preferably about 1 to 12 ml, and more preferably about 2 to 10 ml. The amount can appropriately be increased or decreased while observing the state of the injury lesion. The application to the surface of the composition containing a monovalent metal salt of alginic acid may take place as long as, for example, several seconds to 10-odd seconds.

Furthermore, the composition of the present invention may contain a cross-linking agent that promotes gelation due to the difference in time or temperature or change in the environment such as contact with the calcium ion in vivo so that the composition of the present invention can keep a solution state before the administration and gelates by itself after the administration in vivo. Examples of such cross-linking agents include calcium gluconate, $CaSO_4$ and calcium alginate.

Here, when the cross-linking agent contains calcium, a higher calcium concentration is known to develop gelation faster and form harder gel. Since, however, calcium has cytotoxicity, when the concentration is too high, it may adversely affect the cartilage regeneration effect of the composition for cartilage regeneration of the present invention. Accordingly, when, for example, a $CaCl_2$ solution is used in order to cure the surface of a composition containing a monovalent metal salt of alginic acid, the concentration is preferably 25 mM to 200 mM, and more preferably 50 to 100 mM.

Since the surface of the composition of the present invention is gelated with a cross-linking agent or the whole composition is gelated by mixing the composition with a cross-linking agent in advance upon applying the composition to the cartilage injury lesion, the composition of the present invention is cured at the affected area and can be located at the applied cartilage injury lesion in a closely attached state. Thus, the component (b) can allow migration and accumulation of the host-derived cells to the affected area. In addition, since the composition of the present invention is closely attached to the cartilage injury lesion, the cartilage regeneration effect, in particular, the hyaline cartilage regeneration effect, of the composition of the present invention is more strongly produced.

8. Application of Composition for Cartilage Regeneration to Cartilage Injury Lesion A composition for cartilage regeneration of the present invention can be applied to a cartilage injury lesion of human or an organism other than human, for example, a non-human mammal such as bovine, monkey, avian, cat, mouse, rat, guinea pig, hamster, pig, dog, rabbit, sheep or horse to promote regeneration of the cartilage.

The composition for cartilage regeneration of the present invention is preferably, in a liquid state with fluidity, namely, a solution state. According to the present invention, the phrase "having fluidity" means to have a property of changing its form into indefinite shapes. For example, the composition preferably has fluidity so that it can be included in a syringe or the like and injected into an affected area. The composition of the present invention in a solution state can also readily be applied to a cartilage injury lesion with a syringe, a gel pipette, a specialized syringe or the like. In addition, it allows the composition to adapt to a injury or defect lesion of any shape, and allows the composition to fill or make contact with the whole defect lesion.

In some embodiments, the composition of the present invention can cover the entire injury lesion, has good adhesiveness to the cartilage defect lesion and can easily make contact with cells or tissues of the injury lesion of an organism. Accordingly, component (b) can easily promote migration of the host-derived cells to the affected area. In some embodiments, the composition of the present invention applied to the injury lesion fuses to the tissues of the organism such that it is indistinguishable at the applied site in about four weeks or so following the application, with high compatibility to the organism.

When the viscosity of the composition for cartilage regeneration of the present invention is too high such that it is difficult to apply it with a syringe to fill in a cartilage defect lesion, a pressurized or an electrically-powered syringe may be used. Instead of using a syringe or the like, the composition may also be applied to the cartilage injury lesion, for example, with a spatula, a stick or the like. When the composition is injected with a syringe, for example, a 16 G to 18 G needle is preferably used. The composition of the present invention is used such that it is directly injected into a cartilage defect lesion preferably under an arthroscope or an endoscope with a syringe, a gel pipette, a specialized filling instrument or the like. Alternatively, an affected area may be exposed by a known surgical procedure, for example, arthrotomy by medial parapatellar approach before directly injecting the composition into the cartilage defect lesion with a syringe, a gel pipette, a specialized filling instrument or the like but since the composition of the present invention can be applied to the cartilage injury lesion by a simple procedure with a syringe or the like, there is no need of widespread arthrotomy.

An amount of the composition for cartilage regeneration of the present invention to be applied is not particularly limited and may be determined according to the size of the cartilage defect lesion or the size of the hole formed in the injury lesion where the composition is to be applied. When the composition is directly injected into the cartilage defect lesion, the amount is, for example, 0.05 to 10 ml, and more preferably 0.1 to 2 ml. Preferably, the composition is applied to the cartilage injury lesion by injection so as to sufficiently fill in the cavity volume of the affected area.

A composition for cartilage regeneration of the present invention may also contain, if necessary, other pharmaceutically active ingredients and components ordinarily used in pharmaceuticals, such as commonly used stabilizers, emulsifiers, osmotic pressure adjusters, buffers, isotonic agents, preservatives, pain relievers or colorants.

In one embodiment of the present invention, the composition of the present invention does not contain any component that exerts pharmacological action to the cartilage, other than a monovalent metal salt of low endotoxin alginic acid and SDF-1. Such a composition of the present invention can exert a sufficient cartilage regeneration effect.

Furthermore, in some embodiments, the composition for cartilage regeneration of the present invention does not contain cells, especially cells for cartilage regeneration. Examples of cells for cartilage regeneration include, for example, stem cells and stromal cells, where their source is not particularly limited but examples thereof include bone marrow, adipose cells and umbilical cord blood. Particular examples include mesenchymal stem cells and bone marrow mesenchymal stromal cells. Additional examples include cells such as cartilage precursor cells, chondrocytes, synovial cells, hematopoietic stem cells and ES cells. The phrase "to contain cells for cartilage regeneration" refers to addition of cells that are prepared by a process in which cells of interest are collected and concentrated from bone marrow or the like or a process where the cells are cultured to increase the amount thereof. Specifically, the phrase means that cells for cartilage regeneration is contained, for example, for $1\times10^5$ cells/ml or more.

The composition for cartilage regeneration of the present invention may also contain a factor for promoting cell growth. Examples of such factors include BMP, FGF, VEGF, HGF, TGF-$\beta$, IGF-1, PDGF, CDMP, CSF, EPO, IL and IF. These factors may be produced by a recombinant method or purified from a protein composition.

In one embodiment of the present invention, the composition of the present invention does not contain these growth factors. Even when the composition does not contain such growth factors, regeneration of the cartilage is sufficiently favorable.

In some embodiments of the present invention, the composition of the present invention does not contain any scaffold material for cells except (a) a monovalent metal salt of low endotoxin alginic acid. A "scaffold material for cells" refers to a material that serves as a scaffold for migrated cells that contribute to cartilage regeneration, for example, host-derived mesenchymal stem cells, to differentiate and/or to proliferate. Examples of such scaffold materials include those described in page 5, line 29 to page 6, line 16 of WO2010/048418 (except a monovalent metal salt of low endotoxin alginic acid or a gel obtained by curing said monovalent metal salt).

Furthermore, the present invention also provides use of (a) a monovalent metal salt of low endotoxin alginic acid and (b) SDF-1 for producing a composition for cartilage regeneration.

In addition, the present invention provides a combination of (a) a monovalent metal salt of low endotoxin alginic acid and (b) SDF-1 used for cartilage regeneration.

9. Therapeutic Method

The present invention further provides a method of cartilage regeneration by using the above-described composition for cartilage regeneration of the present invention. Specifically, the present invention provides a cartilage regeneration method comprising the step of applying a composition wherein (a) a monovalent metal salt of low endotoxin alginic acid and (b) SDF-1 are used in combination, to a cartilage injury lesion. More specifically, the present invention provides a cartilage regeneration method comprising the step of applying a therapeutically effective amount of a composition wherein (a) a monovalent metal salt of low endotoxin alginic acid and (b) SDF-1 are used in combination, to a cartilage injury lesion of a subject in need thereof.

The phrases "used in combination" and "apply to a cartilage injury lesion" are as described above.

A "subject" refers to human or an organism other than human, for example, a non-human mammal such as bovine, monkey, avian, cat, mouse, rat, guinea pig, hamster, pig, dog, rabbit, sheep or horse. A method for applying a composition for cartilage regeneration of the present invention to a cartilage injury lesion is not particularly limited. For example, the composition may directly be injected into a cartilage defect lesion under an arthroscope or an endoscope, with a syringe, a gel pipette, a specialized filling instrument or the like. Alternatively, an affected area may be exposed, for example, by a known surgical procedure such as arthrotomy by medial parapatellar approach or the like and then the composition can directly be injected into the cartilage defect lesion with a syringe, a gel pipette, a specialized filling instrument or the like.

Moreover, a co-administered drug, for example, an antibiotic such as streptomycin, penicillin, tobramycin, amikacin, gentamicin, neomycin or amphotericin B or an anti-inflammation drug such as aspirin, a non-steroidal analgesic antipyretic drug (NSAID) or acetaminophen may be administered before, simultaneously or after applying the composition of the present invention to the cartilage injury lesion. These drugs may also be used by being mixed with the composition of the present invention.

One or more holes may be formed in a cartilage injury lesion so that the composition of the present invention is injected into the holes. Furthermore, one or more holes may further be formed into a cartilage defect lesion for the same purpose.

For example, in the case where an affected area is exposed by a surgical procedure, a power drill, steel wire or the like may be used to create a plurality of defects (full-thickness defects) that reach the subchondral bone with a relatively small diameter of, for example, about 1.5 mm in a cartilage defect lesion having remaining cartilage before injecting the composition of the present invention. Creation of full-thickness defects allows the cartilage precursor cells in the bone marrow to easily migrate toward the cartilage defect lesion. Cell migration and cartilage regeneration are promoted due to the effect of the composition of the present invention and thus the cartilage regeneration effect can be enhanced.

The cartilage injury lesion as the affected area is preferably subjected to a necessary pretreatment before being applied with the composition of the present invention. If necessary, the affected area is washed. The phrase "to wash the affected area" refers to removal of blood components, other unwanted tissues and the like, for example, with physiological saline from the site where the composition of the present invention is to be applied. After washing the affected area, the remaining unwanted fluid component are preferably dried by wiping off or the like before applying the composition of the present invention.

After applying the composition of the present invention to the cartilage injury lesion, a cross-linking agent is preferably applied to the surface of said composition. By applying the cross-linking agent to the surface of the composition, the composition of the present invention is cured in the affected area. Furthermore, the excessive amount of cross-linking agent remaining in the affected area may be washed and removed with physiological saline or the like.

All of these steps can be performed under an arthroscope.

According to a preferred embodiment of a cartilage regeneration method of the present invention, a cartilage injury lesion or a cartilage disease can be treated.

10. Kit for Cartilage Regeneration

The present invention further provides a kit for cartilage regeneration. The kit comprises a formulation containing at least component (a) of the composition for cartilage regeneration of the present invention. The kit may further include a cross-linking agent, a solvent, a syringe, a gel pipette, a specialized filling instrument, instruction and the like. A preferable example of such a kit has an alginic acid solution enclosed in one chamber and SDF-1 powder in the other chamber of the integrally molded two chambers of a syringe which are separated by a partition. The partition between the two chambers is made such that it can readily be opened upon use so that both contents can be mixed/dissolved upon use. Other exemplary kit has a composition for cartilage regeneration enclosed in a pre-filled syringe so that the composition can directly be used upon administration without the need of manipulation for preparation. Other exemplary kit has an alginic acid solution and a cross-linking agent enclosed in separate syringes, which are included in one package. The kit may further include a co-administered drug, for example, an antibiotic such as streptomycin, penicillin, tobramycin, amikacin, gentamicin, neomycin or amphotericin B or an anti-inflammation drug such as aspirin, a non-steroidal analgesic antipyretic drug (NSAID) or acetaminophen.

By using this kit, cartilage regeneration treatment can be carried out smoothly.

All publications cited herein, such as prior art documents, unexamined patent applications, patent publications and other patent documents, are incorporated in their entirety herein by reference. In addition, the present specification incorporates the disclosed contents of the claims, specification and drawings of Japanese Patent Application No. 2011-181662 (filed on Aug. 23, 2011), which serves as the basis for claiming priority of the present application.

Hereinafter, the present invention will be specifically described by means of examples, although the present invention is not limited to these examples.

Example 1

Expression of SDF-1 Protein in Osteochondral Defect Models

An osteochondral defect model of a rabbit knee joint was used to examine change in the expression of SDF-1 protein at a injury site with time by immunohistostaining.

15-week-old female Japanese white rabbits (weight 2.6 to 2.9 kg) were used to prepare osteochondral defect models. Anesthesia was performed by intravenous administration of 0.05 mg/kg pentobarbital and inhalation anesthesia of isoflurane. An antibiotic (penicillin G, Meiji Co., Ltd.) was intramuscularly administered. After incision in the skin of about 2 cm, patella was turned over by medial parapatellar approach to expand the patellar surface of the femur. A power drill (Rexon, Kawasaki) was used to create full-thickness osteochondral defects (diameter of 4.5 mm and depth of 3 mm) that reach the subchondral bones in the patellar surfaces of femurs of both knees. A sham surgery group (control) received the same surgery except the creation of the full-thickness osteochondral defect. The full-thickness osteochondral defects provide a favorable model of a cartilage injury lesion. Additional defect in the bone layer allows observation of the effects on the subchondral bone formation and the tide mark (that forms boundary between cartilage and bone).

At each of the time points, i.e., three hours, one week, two weeks and four weeks following the surgery, the rabbits as the subjects were euthanized by intravenous injection of an excessive dose of pentobarbital. The limbs were resected with a power saw to obtain knee specimens.

In order to confirm the expression of SDF-1 protein at the cartilage injury lesion, immunohistostaining was performed using a mouse anti-SDF-1 monoclonal antibody (R&D Systems, Inc.). The specimen was immobilized with a 10% formalin solution containing 4% phosphate buffer and embedded in paraffin. A sample was prepared with a section from the center of the osteochondral defect created part with a thickness of 5 μm.

The specimens were freeze-fractured for Western blotting, homogenized in 8M urea, 50 mM phosphate and 10 mM Tris (pH 8.0) buffer, and added with EDTA (50 mM). After 24 hours of incubation at room temperature, the homogenates were centrifuged to obtain supernatants. The expression level of SDF-1 protein was assessed by Western blotting using a mouse anti-SDF-1 monoclonal antibody.

Results from the immunohistostaining indicated that expression of SDF-1 protein at the injury site was found a week following the creation of the full-thickness osteochondral defects (FIGS. 1B and 1I). On the other hand, expression of SDF-1 protein was not confirmed three hours, two weeks and four weeks following the injuries (FIGS. 1A, 1C and 1D). In the sham operation group, expression of SDF-1 protein was not observed at any time point (FIGS. 1E-1H). Western blotting also indicated that expression of SDF-1 protein was observed only in the tissues of a week following the injuries, which coincide with the results from the immunohistostaining (FIG. 1J). This experiment revealed expression of SDF-1 protein at a osteochondral injury lesion for the first time Example 2

Application of Alginic Acid Gel to Rabbit Osteochondral Defect Models (2-1) Alginic Acid A low endotoxin sodium alginate (Sea Matrix (sterilized), with a molecular weight of about 1,700,000 Da, distributed from Mochida International Ltd.) was used. 12.5 ml of deionized water sterilized by a filter procedure was added to 0.25 g of sodium alginate (lyophilized product) to obtain a 2% sodium alginate solution that is to be used in the experiment. The endotoxin level of the low endotoxin sodium alginate was 5.76 EU (endotoxin unit)/g. The endotoxin level of food grade (commercial grade) sodium alginate (Wako Pure Chemical Industries, Ltd., sodium alginate 500, 199-09961) is 75,950 EU/g, and thus sodium alginate with an extremely low endotoxin level is used in this experiment.

(2-2) Preparation of Models

Rabbit osteochondral defect models were prepared by the procedure described in Example 1. The prepared full-thickness osteochondral defects were washed with physiological saline so that no hematoma exists at the defect lesion. Thereafter, the defect lesion was filled with a 2% sodium alginate solution. The preparation was carried out for the following four groups where n=10.

1) Untreated group (without administration of alginic acid; indicated as "Defect" in the figure)

2) Alginic acid group
(a 2% sodium alginate solution containing 10 μg/ml of BSA as a protein control for SDF-1; indicated as "Vehicle" in the FIG.

3) Alginic acid+SDF-1 administration group
(a 2% sodium alginate solution containing 10 μg/ml of SDF-1 (Human SDF-1α; Miltenyi Biotec Inc., Auburn, Calif.); indicated as "SDF-1" in the FIG.

4) Alginic acid+AMD3100 administration group
(a 2% sodium alginate solution containing 250 μg/ml of AMD3100 (CXCR4 antagonist, Sigma-Aldrich, Saint Louis, Mo.); indicated as "AMD3100" in the figure)

Since the sodium alginate solution has high viscoelasticity, it did not flow out from the defect lesion. A 100 mM calcium hydrochloride (Wako Pure Chemical Industries, Ltd.) solution was applied onto the surface of the sodium alginate solution injected into the defect lesion, left to stand for 10 seconds to confirm curing of the alginic acid. No other anchoring was added to the site for injecting the sodium alginate solution. Articular capsule, fascia and skin were sutured with a 4-0 nylon thread. No anchor splint was used and the rabbits were allowed to freely move in the cage.

(2-3) Macroscopic Findings, Histological Assessment, Immunohistological Assessment The rabbits were sacrificed under high concentration intravenous anesthesia 4 and 16 weeks after the surgery. The limbs were resected with a power saw to obtain knee specimens. Then, their pictures were taken with a digital camera for assessment for macroscopic findings. The specimens for histological assessment and immunohistological assessment were prepared in the same manner as Example 1. Samples were prepared using sections from the center of the osteochondral defect created part with a thickness of 5 μm. The samples were stained with Safranin-O and H-E Immunohistostaining was carried out by staining with an anti-type I collagen antibody and an anti-type II collagen antibody (Fuji Pharma Co. Ltd.). The macroscopic and histological findings were scored according to the method of Niederrauer et al. (Biomaterial 21 (2000) 2561-2574). Scoring was carried out by an independent blind observer.

(2-3-1) Macroscopic Findings

Infection or inflammation reaction such as foreign-body reaction was found in none of the knees. Four weeks after the surgery, the implanted alginic acid gel remained at the defect lesions for the alginic acid group and the alginic acid+AMD3100 administration group (FIGS. 2B and 2D). For the untreated group and the alginic acid+AMD3100 administration group, roughness and mild dents on the surface of the repaired tissues and incomplete fusion with the adjacent cartilage were found 16 weeks after the surgery (FIGS. 2A, 2D, 2E and 2H).

Meanwhile, for the alginic acid group and the alginic acid+SDF-1 administration group, the surface was smooth and fusion with the adjacent cartilage was improved 16 weeks after the surgery (FIGS. 2F and 2G). For the alginic acid+SDF-1 administration group, the defect lesion was partially filled with white glossy solid hyaline cartilage-like tissues four weeks after the surgery (FIG. 2C), and was almost replaced by hyaline cartilage-like tissues 16 weeks after the surgery (FIG. 2G).

With respect to the average macroscopic scores, significant improvement was observed 16 weeks than 4 weeks after the surgery in all of the groups (FIGS. 2I and 2J). Regarding comparison between the groups, macroscopic scores of the alginic acid+SDF-1 administration group 4 weeks after the surgery were significantly higher than those of the other groups (FIG. 2I). The macroscopic scores of the alginic acid+AMD3100 administration group 4 weeks after the surgery was significantly lower than those of the alginic acid group (FIG. 2I). The macroscopic scores of the alginic acid+SDF-1 administration group 16 weeks after the surgery were significantly higher than those of the other groups (FIG. 2J).

(2-3-2) Histological and Immunohistological Findings (4 Weeks after Surgery)

The repaired tissues of the untreated group and the alginic acid+AMD3100 administration group were fibrous tissues mainly consisting of type I collagen (FIGS. 3A, 3D, 3E, 3H, 3I and 3L). Meanwhile, in the alginic acid group and the alginic acid+SDF-1 administration group, the defect lesions were partially repaired with hyaline cartilage-like tissues that contain glycosaminoglycan and type II collagen (FIGS. 3B, 3C, 3J and 3K). In both groups, the repaired tissue partially contained type I collagen (FIGS. 3F and 3G). In the alginic acid group, crack was found in the defect lesion (FIG. 3B). None of the groups showed formation of normal subchondral bone, smooth cartilage surface or complete tide mark (that forms boundary between cartilage and bone) 4 weeks after the surgery (FIGS. 3A-D).

The average histological score of the alginic acid+SDF-1 administration group was significantly higher than those of other groups (FIG. 3M).

(2-3-3) Histological and Immunohistological Findings (16 Weeks after Surgery)

The untreated group resulted in repair with only fibrous tissue, with multiple cracks and severe breakage in the surface (FIGS. 4A, 4E and 4I). The alginic acid group and the alginic acid+AMD3100 administration group gave repaired images showing weak staining of type I collagen and type II collagen (FIGS. 4B, 4D, 4F, 4H, 4J and 4L). Regeneration of the subchondral bone was promoted in the alginic acid group than in the alginic acid+AMD3100 administration group (FIG. 4B). While crack was observed at the boundary with cartilage adjacent to the defect lesion in the alginic acid+AMD3100 administration group (FIG. 4D), no crack was observed in the alginic acid group (FIG. 4B). Meanwhile, almost normal hyaline cartilage regeneration was observed in the alginic acid+SDF-1 administration group, which was associated with abundant glycosaminoglycan content, strong type II collagen staining, formation of normal subchondral bone, smooth cartilage surface and complete tide mark (FIGS. 4C and 4K). Type I collagen staining was not found in the cartilage layer (FIG. 4G). Neoplastic cartilage tissue showed good fusion with the adjacent cartilage and bone (FIG. 4C).

The histological score of the alginic acid group and the alginic acid+SDF-1 administration group significantly improved 16 weeks than 4 weeks after the surgery (FIGS. 3M and 4M). The histological scores of the alginic acid+SDF-1 administration group 16 weeks after the surgery were significantly higher than those of the other groups (FIG. 4M). The histological scores of the alginic acid group were significantly superior over those of the untreated group (FIG. 4M). No significant difference was found in the scores between the untreated group and the alginic acid+AMD3100 administration group.

An alginic acid gel was applied to rabbit osteochondral defect models in the same method as described in (2-1) and (2-2) except that an aqueous solution was prepared by adding 6.25 mL of water to 0.25 g of low endotoxin sodium alginate in (2-1), and that a serum collected from the treated rabbit was added to this aqueous solution in a 1:1 volume to obtain a 2% sodium alginate solution and this was administered to the rabbit osteochondral defect models in (2-2) (alginic acid+autologous blood group). As a result, the macroscopic findings, histological findings and immunohistological findings of the alginic acid+autologous blood group were comparable to those of the alginic acid group.

(2-4) Mechanical Assessment

The knee specimens 4 and 16 weeks after the surgery from each group were used to assess the mechanical strength of the repair tissue. Comparison was made to normal knee specimens as a control group. A rod with a hemispherical chip having a diameter of 2.5 mm was vertically pressed against the surfaces of the samples at a speed of 10 mm/min to determine the compression moduli thereof based on the initial slope of the stress-strain curve. The results are shown in Table 1.

TABLE 1

| Group | 4 weeks (MPa) | 16 weeks (MPa) |
| --- | --- | --- |
| Defect | $0.66 \pm 0.08^{\dagger}$ | $0.59 \pm 0.11^{\dagger}$ |
| Vehicle | $0.50 \pm 0.16^{\dagger}$ | $1.82 \pm 0.28^{**,\dagger\dagger}$ |
| SDF-1 | $0.89 \pm 0.05^{\dagger}$ | $2.34 \pm 0.38^{*}$ |
| AMD3100 | $0.60 \pm 0.93^{\dagger}$ | $1.89 \pm 0.18^{**,\dagger\dagger}$ |
| Normal cartilage | | $2.89 \pm 0.25$ |

Mean ± SEM.
*$p < 0.001$ vs. Defect at the same time,
**$p < 0.01$ vs.Defect at the same time,
$^{\dagger}p < 0.001$ vs. Normal knee,
$^{\dagger\dagger}p < 0.05$ vs. Normal knee Four weeks after the surgery, the compression moduli of the repair tissues of all of the groups were lower than the compression modulus of the cartilage tissue of the normal knee specimen (each group n=5, Table 1). No significant different was found among the untreated group, the alginic acid group, the alginic acid+SDF-1 administration group and the alginic acid+AMD3100 administration group. Other than the untreated group, the compression moduli significantly improved 16 weeks after the surgery than 4 weeks after the surgery. The compression moduli of the alginic acid group and the alginic acid+AMD3100 administration group 16 weeks after the surgery were significantly superior over that of the untreated group. The compression modulus of the alginic acid+SDF-1 administration group significantly improved as compared to that of the untreated group, reached about 80% of the normal cartilage and no significant difference was found with the normal cartilage.

(2-5) Assessment of SDF-1 Dosage

In order to examine the SDF-1 dosage, three alginic acid+SDF-1 administration groups with the SDF-1 concentrations of 1, 10 and 100 μg/ml were prepared in the same manner as in (2-2) and they were compared to the alginic acid group. In the same manner as in (2-3), a macroscopic assessment, a histological assessment and an immunohistological assessment were carried out. The assessments took place 4 and 12 weeks after the surgery.

With respect to the macroscopic findings 4 weeks after the surgery, good cartilage regeneration was observed for all of the alginic acid+SDF-1 administration groups (1, 10 and 100 μg/ml) as compared to the alginic acid group (FIG. 5).

Referring to the immunohistological images 12 weeks after the surgery (FIG. 6), regeneration by the hyaline cartilage-like tissues was found in both of the alginic acid group and the SDF-1 administration group, while better cartilage regenerations were observed in the alginic acid+SDF-1 administration groups proportional to the SDF-1 concentrations. In the group containing SDF-1 at a high concentration (100 μg/ml), the cartilage tended to become hyperplastic. Considering the regeneration of the subchondral bone, an appropriate SDF-1 concentration for this model seemed to be approximately 1 to 60 μg/ml, and in particular 10 μg/ml.

Example 3

Assessment of In Vivo Cell Homing

After applying the alginic acid+SDF-1 to the osteochondral defect lesion, quantitative assessment was conducted to see how the in vivo cell homing and migration to the injury lesion take place. An alginic acid group, an alginic acid+SDF-1 administration group and an alginic acid+AMD3100 administration group were prepared in the same method as the rabbit osteochondral defect models described in Example 2. Seven days after the surgery, the implanted alginic acid gels were collected and the numbers of cells in the gels were counted. The collected gel was immobilized with 4% phosphate buffered paraformaldehyde for 24 hours and embedded in paraffin to prepare a sample using a section from the center of the gel with a thickness of 5 μm. The samples were stained with H-E (hematoxylin and eosin).

A week after the surgery, more cells were found in the gel of alginic acid+SDF-1 administration group compared to other groups (FIG. 7C). From the quantitative assessment of the cell counts, the cell counts of the alginic acid+SDF-1 administration group were found to be significantly higher than the cell counts of other groups (each group n=5, FIG. 7E). The cell count of the alginic acid group (FIG. 7E, Vehicle) tended to be higher than the cell count of the alginic acid+AMD3100 administration group (FIG. 7E, AMD3100), but it was not of a significant difference. These results indicate that application of alginic acid+SDF-1 (FIG. 7E, SDF-1) to a cartilage injury lesion promoted migration of the host-derived cells to the injury lesion.

Example 4

In Vitro Assessment of Effect of SDF-1 on Behavior of BMSC

Bone marrows were collected from a tibia of a 15-week-old Japanese white rabbit to isolate and culture bone marrow mesenchymal stromal cells (BMSC). Isolation was carried out according to the method of Wakitani et al. (Wakitani S et al., J bone Joint Surg Am, Vol. 76, p 579, 1994). The isolated cells were incubated at 37° C. under humidified 5% $CO_2$ and maintained in monolayer culture.

(4-1) Test for BMSC Migration with SDF-1

A test for BMSC migration with SDF-1 was carried out using CytoSelect™ 96-well cell migration assay (Cell Biolabs, San Diego, Calif.). 100 μl of BMSC culture solution containing $5 \times 10^5$ cells/ml was added to the upper tray while the lower tray was filled with 150 μl of a SDF-1-free or SDF-1-added (concentration 100 ng/ml) medium, incubated at 37° C. under 5% $CO_2$ for 8 hours and the number of the migrated cells were detected by fluorescent labeling.

BMSC migration significantly increased in the SDF-1-added medium than the SDF-1-free medium (n=16, FIG. 8A).

(4-2) Effect of SDF-1 on BMSC Proliferation

Proliferation and differentiation of BMSC were tested by embedding BMSC in alginic acid gel beads. The cells were suspended in a 2% sodium alginate solution. The suspension was dripped in a $CaCl_2$ solution with a pipette for gelation. Ten minutes later, the resulting microcapsules were washed twice with Ca/Mg-free PBS and once with DMED-HG. The resulting beads contained $1 \times 10^6$ cells per 40 μl of beads.

The alginic acid gel beads containing 10 μg/ml of SDF-1 or 250 μg/ml of AMD3100 were cultured in DMED-HG containing 10% FBS and 1% antibiotics for 3 hours, 1 day, 2 days, 3 days and 7 days. The cells collected from the alginic acid gel beads were washed with PBS for three times, incubated in 50 mM EDTA (Gibco BRL laboratories) at 37° C. under 5% $CO_2$. Ten minutes later, the cells were centrifuged at 1,500 g for 5 minutes for cell collection and the number of live cells was counted with Cell Counting Kit-8 (Dojindo Laboratories, Tokyo, Japan).

In BMSC proliferation test, no significant difference was found among the alginic acid only group (control), the 10 μg/ml SDF-1-added group and the 250 μg/ml AMD3100-added group (n=5, FIG. 8B).

(4-3) Effect of SDF-1 on BMSC Differentiation

Differentiation into chondrocytes in the alginic acid gel beads was tested by culturing BMSC-containing beads in a DMED-HG medium containing 100 μg/ml sodium pyruvate (ICN Biomedicals, Aurora, Ohio), 40 μg/ml proline (ICN Biomedicals), 50 μg/ml ascorbate-2-phosphate (Wako, Osaka, Japan), $1 \times 10^{-7}$M dexamethasone (ICN Biomedicals), 1% ITS plus mix (Sigma-Aldrich, St. Louis., Mo.), 1% antibiotics and 10 ng/ml recombinant human transforming growth factor α3 (R&D Systems, Minneapolis, Minn.) (dissolved with 4 mM HCl containing 1 μg/ml bovine serum albumin) for 28 days. The medium was exchanged every three days. The beads were washed with PBS, immobilized with 4% phosphate buffered paraformaldehyde for 24 hours and embedded in paraffin to prepare a sample using a section from the center of the gel with a thickness of 5 μm. The samples were stained with Safranin-O and H-E Immunohistostaining was carried out using an anti-type I collagen antibody and an anti-type II collagen antibody (Fuji Pharma Co. Ltd.).

In the test for differentiation of BMSC into chondrocytes, no difference was found among the alginic acid only group, the 10 μg/ml SDF-1-added group and the 250 μg/ml AMD3100-added group.

(4-4) Discussion

From the in vitro tests, considering that the BMSC migration was promoted by SDF-1 and that the application of alginic acid+SDF-1 to the cartilage injury lesion in Example 3 promoted the migration of the host-derived cells to the injury lesion, chemotaxis of SDF-1 seemed to promote migration of stem cells such as host-derived BMSC to the osteochondral injury lesion. On the other hand, SDF-1 was found to show no direct action on the BMSC proliferation and differentiation into chondrocytes. The alginic acid appears to play an important role in the cartilage regeneration by the host-derived cells recruited to the cartilage injury lesion. Specifically, it was found that when a composition of an alginic acid containing SDF-1 is applied to a cartilage injury lesion, SDF-1 promotes migration of host-derived stem cells or the like to the affected area while the alginic acid provides environment suitable for the stem cells or the like to differentiate into chondrocytes and for cartilage regeneration, thereby obtaining a good hyaline cartilage regeneration effect without using graft cells.

The invention claimed is:

1. A method for regenerating cartilage comprising: applying to a cartilage injury lesion a composition which comprises (a) a monovalent metal salt of a low endotoxin alginic acid and (b) stromal cell-derived factor 1 ("SDF-1") in combination, wherein the composition has fluidity, with the proviso that the composition does not comprise TGF-β.

2. The method according to claim 1, wherein the composition is provided in a form of a compounding agent that has both components (a) and (b) mixed and formulated together.

3. The method according to claim 1, wherein the composition is provided in a form of components (a) and (b) separately formulated formulations, and provided in combination as a kit.

4. The method according to claim 1, wherein the composition does not contain a cell growth factor.

5. The method according to claim 1, wherein the SDF-1 is contained in the composition at a concentration from 0.2 μg/ml to 100 μg/ml.

6. The method according to claim 1, wherein the composition is cured by applying a cross-linking agent to the surface of the composition.

7. The method according to claim 6, wherein the cross-linking agent is at least one metal ion compound selected from the group consisting of $Ca^{2+}$, $Mg^{2+}$, $Ba^{2+}$ and $Sr^{2+}$.

8. The method according to claim 1, wherein the monovalent metal salt of alginic acid has a weight-average molecular weight of 500,000 or more in gel filtration chromatography.

9. The method according to claim 1, wherein viscosity of the composition is 400 mPas to 20,000 mPas.

10. The method according to claim 1, wherein the composition does not contain cells for cartilage regeneration.

11. The method according to claim 1, wherein the monovalent metal salt of alginic acid is potassium alginate or sodium alginate.

12. The method according to claim 1, wherein the composition does not contain a scaffold material for cells except (a) the monovalent metal salt of low endotoxin alginic acid.

13. The method according to claim 1, wherein the monovalent metal salt of low endotoxin alginic acid has an endotoxin content of 100 EU/g or less.

14. The method according to claim 1, wherein the method is for treating a cartilage injury lesion or for treating a cartilage disease.

15. The method according to claim 1, wherein the composition does not contain a cross-linking agent.

16. A method for regenerating cartilage comprising: applying to a cartilage injury lesion (a) a monovalent metal salt of low endotoxin alginic acid and (b) SDF-1 in combination, with the proviso that TGF-β is not applied to the cartilage injury lesion.

17. A method for regenerating cartilage comprising: applying to a cartilage injury lesion (a) a formulation comprising monovalent metal salt of low endotoxin alginic acid and (b) a formulation comprising SDF-1 in combination, wherein both formulations have fluidity, with the proviso that neither formulation comprises TGF-β.

18. The method according to claim 17, wherein the formulation (a) and (b) are provided separately.

* * * * *